United States Patent
Adams et al.

(10) Patent No.: US 11,091,542 B2
(45) Date of Patent: Aug. 17, 2021

(54) ANTIBODY MOLECULES WHICH BIND TNF ALPHA

(71) Applicant: UCB BIOPHARMA SRL, Brussels (BE)

(72) Inventors: Ralph Adams, Slough (GB); Pallavi Bhatta, Slough (GB); Emma Dave, Slough (GB); Sam Philip Heywood, Slough (GB); David Paul Humphreys, Slough (GB); Diane Marshall, Slough (GB); Daniel John Lightwood, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 481 days.

(21) Appl. No.: 16/063,133

(22) PCT Filed: Dec. 14, 2016

(86) PCT No.: PCT/EP2016/080984
§ 371 (c)(1),
(2) Date: Jun. 15, 2018

(87) PCT Pub. No.: WO2017/102833
PCT Pub. Date: Jun. 22, 2017

(65) Prior Publication Data
US 2020/0291104 A1    Sep. 17, 2020

(30) Foreign Application Priority Data

Dec. 18, 2015 (GB) ...................... 1522394

(51) Int. Cl.
*C07K 16/24* (2006.01)
*C12N 15/63* (2006.01)
*A61K 39/00* (2006.01)

(52) U.S. Cl.
CPC ............ *C07K 16/241* (2013.01); *C12N 15/63* (2013.01); *A61K 2039/505* (2013.01);
(Continued)

(58) Field of Classification Search
None
See application file for complete search history.

(56) References Cited

U.S. PATENT DOCUMENTS

| 4,741,900 A | 5/1988 | Alvarez et al. |
| 5,219,996 A | 6/1993 | Bodmer et al. |

(Continued)

FOREIGN PATENT DOCUMENTS

| EP | 0239400 A2 | 9/1987 |
| EP | 0380068 A1 | 8/1990 |

(Continued)

OTHER PUBLICATIONS

Aaron L. Nelson. Antibody Fragments Hope and Hype. MAbs, 2(1), 77-83. 2010 (Year: 2010).*

(Continued)

*Primary Examiner* — Joanne Hama
*Assistant Examiner* — Zachary Edward Mazanek
(74) *Attorney, Agent, or Firm* — Marshall, Gerstein & Borun LLP

(57) ABSTRACT

The invention relates to antibody molecules having specificity for TNF alpha, therapeutic uses of the antibody molecules and methods for producing said antibody molecules.

22 Claims, 7 Drawing Sheets
Specification includes a Sequence Listing.

(52) U.S. Cl.
CPC .... *A61K 2039/545* (2013.01); *C07K 2317/24* (2013.01); *C07K 2317/33* (2013.01); *C07K 2317/55* (2013.01); *C07K 2317/565* (2013.01); *C07K 2317/622* (2013.01); *C07K 2317/624* (2013.01); *C07K 2317/92* (2013.01)

(56) References Cited

U.S. PATENT DOCUMENTS

| | | | |
|---|---|---|---|
| 5,585,089 | A | 12/1996 | Queen et al. |
| 5,667,425 | A | 9/1997 | Pineau et al. |
| 5,919,452 | A | 7/1999 | Le et al. |
| 6,284,471 | B1 | 9/2001 | Le et al. |
| 7,012,135 | B2 | 3/2006 | Athwal et al. |
| 7,186,820 | B2 | 3/2007 | Athwal et al. |
| 7,402,662 | B2 | 7/2008 | Athwal et al. |
| 7,977,464 | B2 | 7/2011 | Athwal et al. |
| 8,017,739 | B2 | 9/2011 | Eichner et al. |
| 2010/0166778 | A1* | 7/2010 | Cunningham ..... C07K 16/2896 424/173.1 |
| 2013/0330356 | A1* | 12/2013 | Salfeld ............... A61P 31/12 424/158.1 |
| 2014/0044713 | A1* | 2/2014 | De Lau ................ A61K 45/06 424/134.1 |

FOREIGN PATENT DOCUMENTS

| | | |
|---|---|---|
| EP | 0392745 A2 | 10/1990 |
| EP | 0516785 A1 | 12/1992 |
| EP | 0948544 A1 | 10/1999 |
| EP | 1090037 A1 | 4/2001 |
| WO | WO-1986/001533 A1 | 3/1986 |
| WO | WO-1989/000195 A1 | 1/1989 |
| WO | WO-1989/001476 A1 | 2/1989 |
| WO | WO-1990/007861 | 7/1991 |
| WO | WO-1991/009967 A1 | 7/1991 |
| WO | WO-1992/002551 A1 | 2/1992 |
| WO | WO-1992/011383 A1 | 7/1992 |
| WO | WO-1992/022583 A2 | 12/1992 |
| WO | WO-1993/006231 A1 | 4/1993 |
| WO | WO-1996/033204 | 10/1996 |
| WO | WO-1997/029131 | 8/1997 |
| WO | WO-1998/020734 A1 | 5/1998 |
| WO | WO-1998/025971 A1 | 6/1998 |
| WO | WO-1999/064460 A1 | 12/1999 |
| WO | WO-2001/94585 A1 | 12/2001 |
| WO | WO-2002/012502 | 2/2002 |
| WO | WO-2003/031581 A2 | 4/2003 |
| WO | WO-2003/048208 A2 | 6/2003 |
| WO | WO-2003/083061 A2 | 10/2003 |
| WO | WO-2004/051268 A1 | 6/2004 |
| WO | WO-2004/106377 A1 | 12/2004 |
| WO | WO-2005/003169 A2 | 1/2005 |
| WO | WO-2005/003170 A2 | 1/2005 |
| WO | WO-2005/003171 A2 | 1/2005 |
| WO | WO-2005/113605 A1 | 12/2005 |
| WO | WO-2005/117984 A2 | 12/2005 |
| WO | WO-2006/056779 A2 | 6/2006 |
| WO | WO-2007/024715 A2 | 3/2007 |
| WO | WO-2007/060411 | 5/2007 |
| WO | WO-2008/038024 A1 | 4/2008 |
| WO | WO-2008/144753 A2 | 11/2008 |
| WO | WO-2009/040562 A1 | 4/2009 |
| WO | WO-2009/155723 | 12/2009 |
| WO | WO-2010/035012 A1 | 4/2010 |
| WO | WO-2010/121140 | 10/2010 |
| WO | WO-2011/030107 A1 | 3/2011 |
| WO | WO-2011/061492 A2 | 5/2011 |
| WO | WO-2011/083175 | 7/2011 |
| WO | WO-2011/086091 A1 | 7/2011 |
| WO | WO-2012/007880 | 1/2012 |
| WO | WO-2012/051734 | 4/2012 |
| WO | WO-2012/061374 | 5/2012 |
| WO | WO-2012/078878 | 6/2012 |
| WO | WO-2013/011076 | 1/2013 |
| WO | WO-2013/035012 A2 | 3/2013 |
| WO | WO-2013/063110 | 5/2013 |
| WO | WO-2013/063114 | 5/2013 |
| WO | WO-2013/186229 A1 | 12/2013 |
| WO | WO-2014/144299 | 9/2014 |
| WO | WO-2015/144852 | 10/2015 |
| WO | WO-2015/197772 A1 | 12/2015 |
| WO | WO-2016/036918 | 3/2016 |
| WO | WO-2016/202414 A1 | 12/2016 |
| WO | WO-2016/202415 | 12/2016 |
| WO | WO-2017/081320 | 5/2017 |
| WO | WO-2017/102830 | 6/2017 |
| WO | WO-2017/106383 | 6/2017 |

OTHER PUBLICATIONS

Spiess, C., Zhai, Q., and Carter, P. Alternative molecular formats and therapeutic applications for bispecific antibodies. Molecular Immunology, 67 pp. 95-106 Jan. 27, 2015 (Year: 2015).*
Probert, L. TNF and its receptors in the CNS: the essential, the desirable and the deleterious effects. vol. 302 pp. 2-22 Aug. 27, 2015 (Year: 2015).*
Wendling, D. and Prati, C. Paradoxical effects of anti-TNFα agents in inflammatory diseases. Expert Review of Clinical Immunology vol. 10, Issue 1 pp. 159-169 Dec. 10, 2013 (Year: 2013).*
Atzeni, F., et al. Immunogenicity and autoimmunity during anti-TNF therapy. Autoimmunity Reviews vol. 12, Issue 7. pp. 703-708, May 2013 (Year: 2013).*
Ramos-Casals, M., et al. autoimmune diseases induced by TNF-targeted therapies. Best Practice & Research Clinical Rheumatology vol. 22, Issue 5, pp. 847-861 Oct. 2008 (Year: 2008).*
Lawrence Leung and Catherine M Cahill. TNFα and neuropathic pain—a review. Journal of Neuroinflammation, vol. 7 Issue 27, 2010 pp. 1-11 (Year: 2010).*
Katarina Urschel and Iwona Cicha. TNFα in the cardiovascular system: from physiology to therapy. International Journal of Interferon, Cytokine and Mediator Research. vol. 7 pp. 9-25 Jul. 9, 2015 (Year: 2015).*
Ueda, Atsuhisa et al. "Adalimumab in the management of Behçet's disease." Therapeutics and clinical risk management vol. 11 611-9. Apr. 13, 2015 (Year: 2015).*
Jacobi, A., et al. Infliximab in the treatment of moderate to severe atopic dermatitis. Journal of the American Academy of Dermatology vol. 52, Issue 3, Mar. 2005, pp. 522-526 (Year: 2005).*
Sedger, L. and McDermott, M. TNF and TNF-receptors: From mediators of cell death and inflammation to therapeutic giants—past, present and future. Cytokine and Growth Factor Reviews vol. 25, Issue Aug. 4, 2014 pp. 453-472 (Year: 2014).*
FDA. Highlights of prescribing information for Humira. 34 pages Revised Jan. 2008. https://www.accessdata.fda.gov/drugsatfda_docs/label/2008/125057s0110lbl.pdf (Year: 2008).*
FDA. Highlights of prescribing information for Cimzia. 25 pages revised Apr. 2012. https://www.accessdata.fda.gov/drugsatfda_docs/label/2012/125160s0174lbl.pdf (Year: 2012).*
FDA. Highlights of prescribing information for Enbrel. 28 pages Revised Dec. 2012. https://www.accessdata.fda.gov/drugsatfda_docs/label/2012/103795s5503lbl.pdf (Year: 2012).*
FDA. Highlights of prescribing information for Simponi. 33 pages Revised Dec. 2011. https://www.accessdata.fda.gov/drugsatfda_docs/label/2011/125289s0064lbl.pdf (Year: 2011).*
FDA. Highlights of prescribing information for Remicade. 47 pages Revised Feb. 2011. https://www.accessdata.fda.gov/drugsatfda_docs/label/2011/103772s5281lbl.pdf (Year: 2011).*
Adair et al., Therapeutic Antibodies, *Drug Design Reviews.* 2:209-217 (2005).
Altschul et al., Basic local alignment search tool, *J. Mol. Biol.* 215:403-10 (1990).
Altschul et al., Gapped BLAST and PSI-BLAST: a new generation of protein database search programs, *Nucleic Acids Res.* 25:3389-402 (1997).
Angal et al., A single amino acid substitution abolishes the heterogeneity of chimeric mouse human (IgG4) antibody, *Mol. Immunol.* 30:105-8 (1993).

(56) References Cited

OTHER PUBLICATIONS

Babcook et al., A novel strategy for generating monoclonal antibodies from single, isolated lympocytes producing antibodies of defined specificities, *Proc. Natl. Acad. Sci. USA*. 93:7843-8 (1996).
Bloom et al., Epitope mapping and functional analysis of three murine IgG1 monoclonal antibodies to human Tumor Necrosis Factor-Alpha, *Journal of Immunology*, 151:2707-2716 (1993).
Bodmer et al., Preclinical review of anti-tumor necrosis factor monoclonal antibodies, *Critical Care Medicine*. 21:S441-S446 (1993).
Borset et al., The role of the two TNF receptors in proliferation, NF-kappa B activation and discrimination between TNF and LT alpha signaling in the human myeloma cell line OH-2, *Cytokine*. 8:430-438 (1996).
Chapman, PEGylated antibodies and antibody fragments for improved therapy: a review, *Adv. Drug Deliv. Rev.* 54:531-45 (2002).
Chothia et al., Canonical structures for the hypervariable regions of immunoglobulins, *J. Mol. Biol.* 196:901-17 (1987).
Cole et al., The EBV-Hybridoma technique and its application to human lung cancer, *Monoclonal Antibodies and Cancer Therapy*. 77-96 (1985).
Crameri et al., DNA shuffling of a family of genes from diverse species accelerates directed evolution, *Nature*. 391:288-91 (1998).
Dubowchik et al., Receptor-mediated and enzyme-dependent targeting of cytotoxic anticancer drugs, *Pharmacol. Ther.* 83:67-123 (1999).
Elliot et al., Randomized double-blind comparison of chimeric monoclonal antibody to tumor necrosis factor α (cA2) versus placebo in rheumatoid arthritis, *The Lancet*, 344:1105-1110 (1994).
Feldmann et al., Anti-TNFα therapy is useful in rheumatoid arthritis and Crohn's disease: analysis of the mechanism of action predicts utility in other diseases, *Transplantation Proceedings*. 30:4126-4127 (1998).
Feldmann et al., Anti-tumor necrosis factor-α therapy of rheumatoid arthritis, *Advances in Immunology*. 64:283-350 (1997).
Gish et al., Identification of protein coding regions by database similarity search, *Nat. Genet*. 3:266-72 (1993).
Harris, Processing of C-terminal lysine and arginine residues of proteins isolated from mammalian cell culture, *J. Chromatogr. A*. 705:129-34 (1995).
Hellstrom et al., Controlled Drug Delivery, Marcel Dekker, Inc., New York, pp. 623-653 (2nd ed. 1987).
Holliger et al., Engineered antibody fragments and the rise of single domains, *Nat. Biotechnol*. 23:1126-36 (2005).
International Preliminary Report on Patentability, PCT/EP2016/080984 (dated Jun. 19, 2018).
International Search Report and Written Opinion, PCT/EP2016/080984 (dated Apr. 3, 2017).
Kabat et al., Sequences of Proteins of Immunological Interest, Bolt Beranek and Newman Inc., Cambridge, MA (4th ed. 1987).
Kashmiri et al., SDR grafting—a new approach to antibody humanization, *Methods*. 36:25-34 (2005).
Kirschenbaum et al., Antibodies to TNF-α: too little, too late? *Critical Care Medicine*, 26:1625-1626 (1998).
Kohler et al., Continuous cultures of fused cells secreting antibody of predefined specificity, *Nature*. 256:495-7 (1975).
Kozbor et al., The production of monoclonal antibodies from human lymphocytes, *Immunol. Today*. 4:72-9 (1983).
Lesk et al., Computational Molecular Biology, Oxford University Press, New York (1988).
Low et al., Mimicking somatic hypermutation: affinity maturation of antibodies displayed on bacteriophage using a bacterial mutator strain, *J. Mol. Biol*. 260:359-68 (1996).
Madden et al., Applications of network BLAST server, *Methods Enzymol*. 266:131-41 (1996).
Maini et al., Infliximab (chimeric anti-tumour necrosis factor α monoclonal antibody) versus placebo in rheumatoid arthritis patients receiving concomitant methotrexate: a randomized phase III trial, *The Lancet*, 354:1932-1939 (1999).
Marks et al., By-passing immunization: building high affinity human antibodies by chain shuffling, *Biotechnology*. 10:779-83 (1992).
Meager et al., Preparation and characterization of monoclonal antibodies directed against antigenic determinants of recombinant human tumour necrosis factor (rTNF), *Hybridoma*. 6:305-311 (1987).
Mease, Adalimumab: An anti-TNF agent for the treatment of psoriatic arthritis, *Expert Opin. Biol. Therapy*. 5:1491-1504 (2005).
Moreland et al., Etanercept therapy in rheumatoid arthritis: a randomized, controlled trial, *Ann Intern Med*. 130:478-486 (1999).
Nagahira et al., Humanization of a mouse neutralizing monoclonal antibody against tumor necrosis factor-alpha (TNF-alpha), *Journal of Immunological Methods*. 222:83-92(1999).
Patten et al., Applications of DNA shuffling to pharmaceuticals and vaccines, *Curr. Opin. Biotechnol*. 8:724-33 (1997).
Rankin et al., The therapeutic effects of an Engineered human anti-tumour necrosis factor alpha antibody (CDP571) in Rheumatoid arthritis, *British Journal of Rheumatology*. 34:334-342 (1995).
Riechmann et al., Reshaping human antibodies for therapy, *Nature*. 332:323-7 (1988).
Rudikoff et al., Single amino acid substitution altering antigen-binding specificity, *Proc. Natl. Acad. Sci. USA*. 79: 1979-1983 (1982).
Scatchard, The attractions of Proteins for small molecules and ions, *Ann. KY. Acad. Sci*. 51:660-672 (1949).
Shimamoto et al., Monoclonal antibodies against human recombinant tumor necrosis factor: prevention of endotoxic shock, *Immunology Letters*. 17:311-318 (1988).
Stephen et al., Comprehensive pharmacokinetics of a humanized antibody and analysis of residual anti-idiotypic responses, *Immunology*. 85:668-674 (1995).
Thoma et al., Identification of a 60-kD tumor necrosis factor (TNF) receptor as the major signal transducing component in TNF responses, *The Journal of Experimental Medicine*. 172:1019-1023 (1990).
Thompson et al., Affinity maturation of a high-affinity human monoclonal antibody against the third hypervariable loop of human immunodeficiency virus: use of phage display to improve affinity and broaden strain reactivity, *J. Mol. Biol*. 256:77-88 (1996).
Thorpe et al., The preparation and cytotoxic properties of antibody-toxin conjugates, *Immunol. Rev*. 62:119-58 (1982).
Toussirot, Eric et al., "The use of TNF-α blocking agents in rheumatoid arthritis: an overview", *Expert Opin. Pharmacother*. 5:581-594 (2004).
Vaughan et al., Human antibodies by design, *Nat. Biotechnol*. 16:535-9 (1998).
Verma et al., Antibody engineering: comparison of bacterial, yeast, insect and mammalian expression systems, *J. Immunol. Methods*. 216:165-81 (1998).
Von Heinje, Sequence Analysis in Molecular Biology, Academic Press (1987).
Wherry et al., Tumor necrosis factor and the therapeutic potential of anti-tumor necrosis factor antibodies, *Critical Care Medicine*. 21:S436-S440 (1993).
Williams et al., Anti-tumor necrosis factor ameliorates joint disease in murine collagen-induced arthritis, *Proc. Natl. Acad. Sci. USA*. 89:9784-9788 (1992).
Wolff et al., Monoclonal antibody homodimers: enhanced antitumor activity in nude mice, *Cancer Res*. 53:2560-5 (1993).
Yang et al., CDR walking mutagenesis for the affinity maturation of a potent human anti-HIV-1 antibody into the picomolar range, *J. Mol. Biol*. 254:392-403 (1995).
Zhang et al., PowerBLAST: a new network BLAST application for interactive or automated sequence analysis and annotation, *Genome Res*. 7:649:56 (1997).

\* cited by examiner

Figure 1

(a) CDR sequences of antibody 2109

| | | |
|---|---|---|
| CDRH1: | GYTFTDNYIH | (SEQ ID NO:1) |
| CDRH2: | YINPSSAYAHYNEKFKT | (SEQ ID NO:2) |
| CDRH3: | RYYSAMPFAY | (SEQ ID NO:3) |
| CDRL1: | RASEDIYSGLA | (SEQ ID NO:4) |
| CDRL1: | RASEDIYNGLA | (SEQ ID NO:5) |
| CDRL2: | DSSTLHT | (SEQ ID NO:6) |
| CDRL2: | NSNTLHT | (SEQ ID NO:7) |
| CDRL2: | NSSTLHT | (SEQ ID NO:8) |
| CDRL2: | DSNTLHT | (SEQ ID NO:9) |
| CDRL3: | QQNYDFPLT | (SEQ ID NO:10) |

(b)    Light Chain variable region of antibody 2109 gL18 (SEQ ID NO:11) (unmutated*)
DIQMTQSPSSLSASVGDRVTITCRASEDIYSGLAWYQQKPGKVPKLLIYDSSTLHTGVPSRF
SGTGSGTDYTLTISSLQPEDVATYFCQQNYDFPLTFGQGTKLEIKRT (c)    Heavy Chain variable region of antibody 2109 gH2 (SEQ ID NO:12) (unmutated*)
EVQLVESGGGLVKPGGSLRLSCAASGYTFTDNYIHWVRQAPGKGLEWIGYINPSSAYAHYNE
KFKTRFTISVDKAKNSAYLQMNSLRAEDTAVYYCTRRYYSAMPFAYWGQGTLVTVSS (d) DNA encoding Light Chain variable region of antibody 2109 gL18 (SEQ ID NO:13) (unmutated*)
gatatacagatgacccaatcaccaagctctctgagtgcttccgttggcgatcgcgttacaattacctgccgagctagcgaggatatatac
tcaggactggcctggtaccagcaaaagcctggcaaagtgcctaagctcctgatctacgactccagtaccctgcacactggtgtgccaa
gccgctttagcggaactggatctggaaccgactatacactgacgatttcctcactgcaaccggaagacgtggcaacctacttctgtcag
caaaactacgacttccccttgacgtttgggcaaggggacaaagctggagatcaaacgtacc (e) DNA encoding Heavy Chain variable region of antibody 2109 gH2 (SEQ ID NO:14) (unmutated*)
gaagttcaactggtcgaaagcggaggtgggctcgtgaaacctggcggatctctgcgattgtcatgtgctgcaagcggctacacgttta
ccgataactatatccactgggtgcgacaagcaccagggaagggactggaatggattggatatattaacccgagctccgcctacgcac
actacaacgagaaattcaagacccgattcaccatctccgtggacaaagccaagaactccgcttacctgcaaatgaactctctgcgggc
cgaagacactgccgtgtattactgcacccgccgatactatagcgctatgcccttttgcctactggggacaagggacactggtcactgtct
caagt (f)  Light Chain variable region of antibody 2109 gL18 (SEQ ID NO:15) (mutated[f])
DIQMTQSPSSLSASVGDRVTITCRASEDIYSGLAWYQQKPGKVPKLLIYDSSTLHTGVPSRF
SGTGSGTDYTLTISSLQPEDVATYFCQQNYDFPLTFGCGTKLEIKRT (g) Heavy Chain variable region of antibody 2109 gH2 (SEQ ID NO:16) (mutated[f])
EVQLVESGGGLVKPGGSLRLSCAASGYTFTDNYIHWVRQAPGKCLEWIGYINPSSAYAHYNE
KFKTRFTISVDKAKNSAYLQMNSLRAEDTAVYYCTRRYYSAMPFAYWGQGTLVTVSS (h) DNA encoding Light Chain variable region of antibody 2109 gL18 (SEQ ID NO:17) (mutated[f])
2109dsvL

Figure 1 (continued)

```
gatatccagatgacccagtcgccgtccagcctctccgcctccgtgggagacagagtgacgat
cacttgcagagcatcagaggacatctactctggccttgcttggtatcagcagaagccgggaa
aggtgcccaaactgctcatctatgactcctcgaccctccacacgggagtgccatcgcgcttc
agcgggaccggatctgggaccgactacaccctgaccatttcatcgctccagccggaggatgt
tgccacttacttctgccaacagaattacgacttcccacttactttggatgtggcactaagc
tcgaaatcaagcgcacc
```

\* i.e. without cysteines engineered for a disulfide bond
ᶠ i.e. with cysteines engineered for a disulfide bond (i) DNA encoding Heavy Chain variable region of antibody 2109 gH2 (SEQ ID NO:18) (mutatedᶠ)

```
gaagtgcagttggtggagtcggggggagggttggtgaagccaggaggatcattgcggttgtc
atgtgcggcttcgggctacactttcactgacaattacattcactgggtgcgacaagcaccag
ggaagtgcctcgaatggattggctacatcaacccgtcaagcgcatacgccattacaacgaa
aagttcaagacccggttcaccatctccgtggataaggcgaaaaacagcgcgtaccttcagat
gaactccctgcgggccgaggataccgccgtttactactgcactagacggtactacagcgcca
tgccgttcgcgtactggggacaaggcactctggtcaccgtgtcgtcg
```

(j) scFv (VH-VL) of antibody 2109 gH2gL18 (SEQ ID NO:19) (unmutated\*)
EVQLVESGGGLVKPGGSLRLSCAASGYTFTDNYIHWVRQAPGKGLEWIGYINPSSAY
AHYNEKFKTRFTISVDKAKNSAYLQMNSLRAEDTAVYYCTRRYYSAMPFAYWGQG
TLVTVSSGGGGSGGGGSGGGGSGGGGSDIQMTQSPSSLSASVGDRVTITCRASEDIYS
GLAWYQQKPGKVPKLLIYDSSTLHTGVPSRFSGTGSGTDYTLTISSLQPEDVATYFCQ
QNYDFPLTFGQGTKLEIKRT (k) DNA encoding scFv (VH-VL) of antibody 2109 gH2gL18 (SEQ ID NO:20) (unmutated\*)

```
gaagttcaactggtcgaaagcggaggtgggctcgtgaaacctggcggatctctgcgattgtcatgtgctgcaagcggctacacgtttaccgataa
ctatatccactgggtgcgacaagcaccagggaagggactggaatggattggatatattaacccgagctccgcctacgcacactacaacgagaa
attcaagacccgattcaccatctccgtggacaaagccaagaactccgcttacctgcaaatgaactctctgcgggccgaagacactgccgtgtatt
actgcacccgccgatactatagcgctatgcccttgcctactggggacaagggacactggtcactgtctcaagtggaggtggcggttctggcggt
ggcggttccggtggcggtggatcgggaggtggcggttctgatatacagatgacccaatcaccaagctctctgagtgcttccgttggcgatcgcgtt
acaattacctgccgagctagcgaggatatatactcaggactggcctggtaccagcaaaagcctggcaaagtgcctaagctcctgatctacgact
ccagtaccctgcacactggtgtgccaagccgctttagcggaactggatctggaaccgactatacactgacgatttcctcactgcaaccggaagac
gtggcaacctacttctgtcagcaaaactacgacttcccccttgacgtttgggcaagggacaaagctggagatcaaacgtacc
```

(l) dsscFv (VH-VL) of antibody 2109 gH2gL18 (SEQ ID NO:21) (mutated ᶠ)
EVQLVESGGGLVKPGGSLRLSCAASGYTFTDNYIHWVRQAPGKCLEWIGYINPSSAY
AHYNEKFKTRFTISVDKAKNSAYLQMNSLRAEDTAVYYCTRRYYSAMPFAYWGQG
TLVTVSSGGGGSGGGGSGGGGSGGGGSDIQMTQSPSSLSASVGDRVTITCRASEDIYS
GLAWYQQKPGKVPKLLIYDSSTLHTGVPSRFSGTGSGTDYTLTISSLQPEDVATYFCQ
QNYDFPLTFGCGTKLEIKRT (m) DNA encoding dsscFv (VH-VL) of antibody 2109 gH2gL18 (SEQ ID NO:22) (mutatedᶠ)

```
Gaagtgcagttggtggagtcggggggagggttggtgaagccaggaggatcattgcggttgtcatgtgcggcttcgggctacactttc
actgacaattacattcactgggtgcgacaagcaccagggaagtgcctcgaatggattggctacatcaacccgtcaagcgcatacgccc
attacaacgaaaagttcaagacccggttcaccatctccgtggataaggcgaaaaacagcgcgtaccttcagatgaactccctgcgggc
cgaggataccgccgtttactactgcactagacggtactacagcgccatgccgttcgcgtactggggacaaggcactctggtcaccgtg
```

Figure 1 (continued)

tcgtcgggaggaggaggctcgggtggaggcggatcgggtggcggagggagcggcggaggcggttcggatatccagatgaccca
gtcgccgtccagcctctccgcctccgtgggagacagagtgacgatcacttgcagagcatcagaggacatctactctggccttgcttggt
atcagcagaagccgggaaaggtgcccaaactgctcatctatgactcctcgaccctccacacgggagtgccatcgcgcttcagcggga
ccggatctgggaccgactacaccctgaccatttcatcgctccagccggaggatgttgccacttacttctgccaacagaattacgacttcc
cacttacttttggatgtggcactaagctcgaaatcaagcgcacc (n) Light Chain variable region of rat antibody 2109 (SEQ ID NO:23)
DIVMTQSPASLSASLGETVTIECRASEDIYNGLAWYQQKPGKSPHLLIYNSNTLHTGV
PSRFSGTGSGTQYSLKINSLQSEDVATYFCQQNYDFPLTFGSGTKLELK (m) Heavy Chain variable region of rat antibody 2109 (SEQ ID NO:24)
EVQLHQSGAALVKPGASVKLSCKTSGYTFTDNYIHWVKQSPGKSLEWIGYINPSSAY
AHYNEKFKTKATLTVDKSTNTAYMELSRLTSEDSATYFCTRRYYSAMPFAYWGQG
TLVTVSS (o) Human VK1 2-1(U) A20 JK2 acceptor framework (SEQ ID NO:25)
DIQMTQSPSSLSASVGDRVTITCRASQGISNYLAWYQQKPGKVPKLLIYAASTLQSGV
PSRFSGSGSGTDFTLTISSLQPEDVATYYCQKYNSAPYTFGQGTKLEIK
\* i.e. without cysteines engineered for a disulfide bond
$^j$ i.e. with cysteines engineered for a disulfide bond (p) Human VH3 1-3 3-21 JH4 acceptor framework (SEQ ID NO:26)
EVQLVESGGGLVKPGGSLRLSCAASGFTFSSYSMNWVRQAPGKGLEWVSSISSSTSY
IYYADSVKGRFTISRDNAKNSLYLQMNSLRAEDTAVYYCARYFDYWGQGTLVTVSS (q) Light Chain variable region of antibody 2109 gL1 (SEQ ID NO:27)
DIQMTQSPSSLSASVGDRVTITCRASEDIYNGLAWYQQKPGKVPKLLIYNSNTLHTG
VPSRFSGTGSGTDYTLTISSLQPEDVATYFCQQNYDFPLTFGQGTKLEIK (r) Heavy Chain variable region of antibody 2109 gH1 (SEQ ID NO:28)
EVQLVESGGGLVKPGGSLRLSCATSGYTFTDNYIHWVRQAPGKGLEWIGYINPSSAY
AHYNEKFKTRFTISVDKAKNSAYLQMNSLRAEDTAVYYCTRRYYSAMPFAYWGQG
TLVTVSS (s) Mouse heavy g1 constant region (SEQ ID NO:30)

AKTTPPSVYPLAPGSAAQTNSMVTLGCLVKGYFPEPVTVTWNSGSLSSGVHTFPAVL
QSDLYTLSSSVTVPSSTWPSETVTCNVAHPASSTKVDKKIVPRDCGCKPCICTVPEVS
SVFIFPPKPKDVLTITLTPKVTCVVVDISKDDPEVQFSWFVDDVEVHTAQTQPREEQF
NSTFRSVSELPIMHQDWLNGKEFKCRVNSAAFPAPIEKTISKTKGRPKAPQVYTIPPPK
EQMAKDKVSLTCMITDFFPEDITVEWQWNGQPAENYKNTQPIMDTDGSYFVYSKLN
VQKSNWEAGNTFTCSVLHEGLHNHHTEKSLSHSPGK (t) Mouse heavy g1 Fab no hinge constant region (SEQ ID NO:31)

AKTTPPSVYPLAPGSAAQTNSMVTLGCLVKGYFPEPVTVTWNSGSLSSGVHTFPAVL
QSDLYTLSSSVTVPSSTWPSETVTCNVAHPASSTKVDKKIVPRDC (u) Mouse light chain constant region (SEQ ID NO:32)

Figure 1 (continued)

RTDAAPTVSIFPPSSEQLTSGGASVVCFLNNFYPKDINVKWKIDGSERQNGVLNSWT
DQDSKDSTYSMSSTLTLTKDEYERHNSYTCEATHKTSTSPIVKSFNRNEC (v) Light chain constant region (SEQ ID NO:33)

RTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC (w) Heavy chain gamma 1 Fab CH1 no hinge constant region (SEQ ID NO:34)

ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSC (x) Heavy chain gamma 1 full length constant region (SEQ ID NO:35)

ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK (y) Heavy chain gamma 4 full length constant region (SEQ ID NO:36)

ASTKGPSVFPLAPCSRSTSESTAALGCLVKDYFPEPVTVSWNSGALTSGVHTFPAVLQ
SSGLYSLSSVVTVPSSSLGTKTYTCNVDHKPSNTKVDKRVESKYGPPCPSCPAPEFLG
GPSVFLFPPKPKDTLMISRTPEVTCVVVDVSQEDPEVQFNWYVDGVEVHNAKTKPR
EEQFNSTYRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLDSDGSFFL
YSRLTVDKSRWQEGNVFSCSVMHEALHNHYTQKSLSLSLGK (z) Heavy chain gamma 4P full length constant region (SEQ ID NO:37)

ASTKGPSVFPLAPCSRSTSESTAALGCLVKDYFPEPVTVSWNSGALTSGVHTFPAVLQ
SSGLYSLSSVVTVPSSSLGTKTYTCNVDHKPSNTKVDKRVESKYGPPCPPCPAPEFLG
GPSVFLFPPKPKDTLMISRTPEVTCVVVDVSQEDPEVQFNWYVDGVEVHNAKTKPR
EEQFNSTYRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLDSDGSFFL
YSRLTVDKSRWQEGNVFSCSVMHEALHNHYTQKSLSLSLGK

\* i.e. without cysteines engineered for a disulfide bond
ƒ i.e. with cysteines engineered for a disulfide bond

Figure 3

HEAVY CHAIN

```
                 1       5        10        15        20        25        30        35        40        45        50  abc  55        60        65        70        75        80  abc  85        90        95       100       105       110
(SEQ ID NO:24)
CA2109           EVQLHQSGAALVKPGASVKLSCKTSGYTFTDNYIHWVKQSPGKSLEWIGYINP   SSAYAHYNEKFKTKATLTVDKSTNTAYMELSRLTSEDSATYFCTRRYYSAMPFAYWGQGTLVTVSS (SEQ ID NO:26)
1-3 3-21         EVQLVESGGGLVKPGGSLRLSCAASGFTFSSYSMNWVRQAPGKGLEWVSSISS   STSYIYYADSVKGRFTISRDNAKNSLYLQMNSLRAEDTAVYYCAR                    YFDYWGQGTLVTVSS (SEQ ID NO:28)
CA2109gH1        EVQLVESGGGLVKPGGSLRLSCAISGYTFTDNYIHWVRQAPGKGLEWIGYINP   SSAYAHYNEKFKTRFTISVDKAKNSAYLQMNSLRAEDTAVYYCTRRYYSAMPFAYWGQGTLVTVSS (SEQ ID NO:12)
CA2109gH2        EVQLVESGGGLVKPGGSLRLSCAASGYTFTDNYIHWVRQAPGKGLEWIGYINP   SSAYAHYNEKFKTRFTISVDKAKNSAYLQMNSLRAEDTAVYYCTRRYYSAMPFAYWGQGTLVTVSS
```

Legend

CA2109 = Rat variable heavy chain sequence 1-3 3-21 = human germline acceptor framework VH3 sequence 1-3 3-21 with JH4

CA2109gH1 & CA2109gH2 = Humanized grafts of CA2109 variable heavy chain using 1-3 3-21 human germline as the acceptor framework.

CDRs are shown in bold/underlined

Donor residues in CA2019gH2 are shown in bold/italic and are highlighted: I48, G49, V71, K73, A78, T93

Figure 4

LIGHT CHAIN

```
                 1         5        10        15        20        25        30        35        40        45        50        55        60        65        70        75        80        85        90        95       100       105
(SEQ ID NO:23)
CA2109           DIVMTQSPASLSASLGETVTIECRASEDIYNGLAWYQQKPGKSPHLLIYNSNTLHTGVPSRFSGTGSGTQYSLKINSLQSEDVATYFCQQNYDFP LTFGSGTKLELK (SEQ ID NO:25)
2-1(U)-A20       DIQMTQSPSSLSASVGDRVTITCRASQGISNYLAWYQQKPGKVPKLLIYAASTLQSGVPSRFSGSGSGTDFTLTISSLQPEDVATYYCKYNSAP YTFGQGTKLEIK (SEQ ID NO:27)
CA2109gL1        DIQMTQSPSSLSASVGDRVTITCRASEDIYNGLAWYQQKPGKVPKLLIYNSNTLHTGVPSRFSG*T*GSGTD*Y*TLTISSLQPEDVATY*F*CQQNYDFP LTFGQGTKLEIK (SEQ ID NO:29)
CA2109gL18       DIQMTQSPSSLSASVGDRVTITCRASEDIYSGLAWYQQKPGKVPKLLIYDSSTLHTGVPSRFSG*T*GSGTD*Y*TLTISSLQPEDVATY*F*CQQNYDFP LTFGQGTKLEIK
```

Legend

CA2109 = Rat variable light chain sequence 2-1 (U)-A20 = human germline acceptor framework sequence VK1 2-1(U) A20 with JK2

CA2109gL1 and CA2109gL18 = Humanized grafts of CA2109 variable light chain using VK1 2-1(U) A20 human germline as the acceptor framework.

CDRs are shown in bold/underlined
Donor residues are shown in bold/italic and are highlighted: T65, Y71, F87

The mutations in CDRL1 and CDRL2 to remove a potential Asparagine deamidation site are shown in bold/underlined and are highlighted: S31, D50, S52

ANTIBODY MOLECULES WHICH BIND TNF ALPHA

CROSS-REFERENCE TO RELATED APPLICATIONS

This is the United States national phase of International Patent Application No. PCT/EP2016/080984, filed Dec. 14, 2016, which claims priority to GB 1522394.4, filed Dec. 18, 2015, each of which is herein incorporated by reference in their entireties.

INCORPORATION OF MATERIALS SUBMITTED ELECTRONICALLY

This application contains, as a separate part of disclosure, a Sequence Listing in computer-readable form (filename: 53149 Seqlisting.txt; Size: 39,654 bytes; created: Jun. 13, 2018), which is incorporated by reference in its entirety.

The disclosure relates to antibodies specific to TNF, formulations comprising the same, use of each in therapy, processes for expressing and optionally formulating said antibody, DNA encoding the antibodies and hosts comprising said DNA.

BACKGROUND

The Tumour Necrosis Factor (TNF) superfamily is a family of proteins that share a primary function of regulating cell survival and cell death. Members of the TNF superfamily share a common core motif, which consists of two antiparallel β-pleated sheets with antiparallel β-strands, forming a "jelly roll"β-structure. Another common feature shared by members of the TNF superfamily is the formation of homo- or heterotrimeric complexes. It is these trimeric forms of the TNF superfamily members that bind to, and activate, specific TNF superfamily receptors.

TNFα is the archetypal member of the TNF superfamily—forming a symmetrical homotrimer. Dysregulation of TNFα production has been implicated in a number of pathological conditions of significant medical importance. For example, TNFα has been implicated in rheumatoid arthritis, inflammatory bowel diseases (including Crohn's disease), psoriasis, Alzheimer's disease (AD), Parkinson's disease (PD), pain, epilepsy, osteoporosis, asthma, systemic lupus erythematosus (SLE) and multiple sclerosis (MS).

Known antagonists of TNF superfamily members are macromolecular and act by inhibiting the binding of the TNF superfamily member to its receptor. Examples of such antagonists include anti-TNFα antibodies, particularly monoclonal antibodies, such as infliximab (Remicade®), adalimumab (Humira®) and certolizumab pegol (Cimzia®), or soluble TNFα receptor fusion proteins, such as etanercept (Enbrel®). These both inhibit soluble TNFα and its interaction with the receptor TNFR1 (responsible for inflammation) and membrane-bound TNFα and its interaction with the receptor TNFR2 (involved in the immune response).

The role of TNFα as a key driver of disease in rheumatoid arthritis (RA) patients is well established. Indeed, anti-TNFα antibodies have transformed patient care and anti-TNFα plus methotrexate is now the current gold standard of care for RA patients.

SUMMARY OF THE DISCLOSURE

Thus in one aspect there is provided an anti-TNF antibody or binding fragment thereof comprising a heavy chain or heavy chain fragment having a variable region, wherein said variable region comprises one, two or three CDRs independently selected from SEQ ID NO: 1, SEQ ID NO: 2 and SEQ ID NO: 3, for example wherein CDR H1 is SEQ ID NO: 1, CDR H2 is SEQ ID NO: 2 and/or CDR H3 is SEQ ID NO: 3.

Thus one embodiment CDR H1 is SEQ ID NO: 1 and CDR H2 is SEQ ID NO: 2, or CDR H1 is SEQ ID NO: 1 and CDR H3 is SEQ ID NO: 3, or CDR H2 is SEQ ID NO: 2 and CDR H3 is SEQ ID NO: 3.

In one embodiment the antibodies or binding fragments according to the present disclosure comprise a light chain or light chain fragment having a variable region, for example comprising one, two or three CDRs independently selected from SEQ ID NO: 4 to 10, in particular wherein CDR L1 has the sequence given in SEQ ID NO: 4 or 5, CDR L2 has the sequence given in SEQ ID NO: 6, 7, 8 or 9 and CDR L3 has the sequence given in SEQ ID NO: 10.

Thus one embodiment CDR L1 is SEQ ID NO: 4 and CDR L2 is SEQ ID NO: 6, 7, 8 or 9 CDR L1 is SEQ ID NO: 5 and CDR L2 is SEQ ID NO: 6, 7, 8 or 9 or CDR L1 is SEQ ID NO: 4 or 5 and CDR L3 is SEQ ID NO: 10; or CDR L2 is SEQ ID NO: 6, 7, 8 or 9 or CDR L1 is SEQ ID NO: 10.

In one embodiment the antibodies or binding fragments according to the present disclosure comprise CDR sequences selected from SEQ ID NOs: 1 to 10, for example wherein CDR H1 is SEQ ID NO: 1, CDR H2 is SEQ ID NO: 2, CDR H3 is SEQ ID NO: 3, CDR L1 is SEQ ID NO: 4 or 5, CDR L2 is SEQ ID NO: 6, 7, 8 or 9 and CDR L3 is SEQ ID NO: 10.

Also provided is an antibody or binding fragment that binds the same epitope as an antibody or binding fragment explicitly disclosed herein.

In one embodiment there is provided an antibody or binding fragment that cross-blocks an antibody or binding fragment explicitly disclosed herein to human TNF, or is cross-blocked from binding human TNF by said antibody.

The disclosure also extends to a polynucleotide, such as DNA, encoding an antibody or fragment as described herein, for example where the DNA is incorporated into a vector.

Also provided is a host cell comprising said polynucleotide.

Methods of expressing an antibody or fragment are provided herein as are methods of conjugating an antibody or fragment to a polymer, such as PEG.

The present disclosure also relates to pharmaceutical compositions comprising said antibodies and fragments.

In one embodiment there is provided a method of treatment comprising administering a therapeutically effective amount of an antibody, fragment or composition as described herein.

The present disclosure also extends to an antibody, fragment or composition according to the present disclosure for use in treatment, particularly in the treatment of an immunological, an autoimmune disorder and/or inflammatory disorders, for example arthritis, such as inflammatory arthritis in particular rheumatoid arthritis or Ankylosing spondylitis.

BRIEF DESCRIPTION OF THE FIGURES

FIG. 1 shows various sequences relating to antibodies and binding fragments of the present disclosure

FIGS. 3/4 show various sequence alignments relating to antibodies and binding fragments of the present disclosure.

DETAILS OF THE DISCLOSURE

Figure 2A:
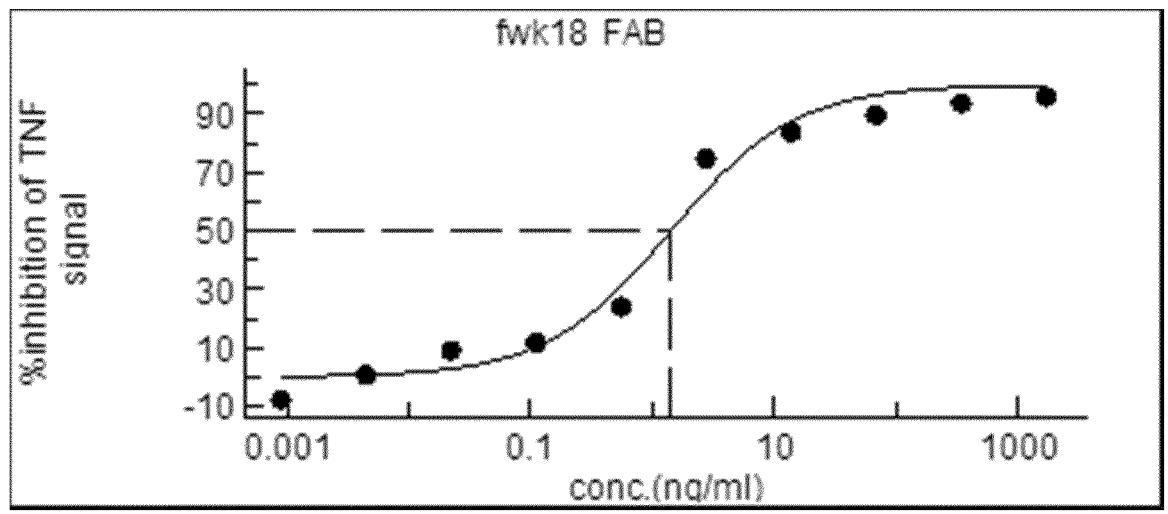
FIG. 2 shows the Titration curves for CA2109 mouse Fab (fwk18 FAB) IgG1 (fwk18 IgG)

TNF as employed herein refers to the cytokine tumor necrosis factor alpha, the human amino acid sequence of which is in UniProt under number P01375.

Antibody molecule as employed herein refers to an antibody or binding fragment thereof.

The term 'antibody' as used herein generally relates to intact (whole) antibodies i.e. comprising the elements of two heavy chains and two light chains. The antibody may comprise further additional binding domains, for example as per the molecule DVD-Ig as disclosed in WO 2007/024715, or the so-called (FabFv)$_2$Fc described in WO2011/030107. Thus antibody as employed herein includes bi, tri or tetravalent full length antibodies.

Binding fragments of antibodies include single chain antibodies (i.e. a full length heavy chain and light chain); Fab, modified Fab, Fab', modified Fab', F(ab')$_2$, Fv, Fab-Fv, Fab-dsFv, single domain antibodies (e.g. VH or VL or VHH), scFv, dsscFv, bi, tri or tetra-valent antibodies, Bis-scFv, diabodies, tribodies, triabodies, tetrabodies and epitope-binding fragments of any of the above (see for example Holliger and Hudson, 2005, Nature Biotech. 23(9): 1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). The Fab-Fv format was first disclosed in WO2009/040562 and the disulphide stabilised versions thereof, the Fab-dsFv was first disclosed in WO2010/035012. Other antibody fragments for use in the present invention include the Fab and Fab' fragments described in International patent applications WO2005/003169, WO2005/003170 and WO2005/003171. Multi-valent antibodies may comprise multiple specificities e.g. bispecific or may be monospecific (see for example WO92/22583 and WO05/113605). One such example of the latter is a Tri-Fab (or TFM) as described in WO92/22583.

In one embodiment there is provided a Fab fragment.

In one embodiment there is provided a Fab' fragment.

A typical Fab' molecule comprises a heavy and a light chain pair in which the heavy chain comprises a variable region V$_H$, a constant domain C$_H$1 and a natural or modified hinge region and the light chain comprises a variable region V$_L$ and a constant domain C$_L$.

In one embodiment there is provided a dimer of a Fab' according to the present disclosure to create a F(ab')$_2$ for example dimerisation may be through the hinge.

In one embodiment the antibody or binding fragment thereof comprises a binding domain. A binding domain will generally comprises 6 CDRs, three from a heavy chain and three from a light chain. In one embodiment the CDRs are in a framework and together form a variable region. Thus in one embodiment an antibody or binding fragment comprises a binding domain specific for antigen comprising a light chain variable region and a heavy chain variable region.

It will be appreciated that one or more (for example 1, 2, 3 or 4) amino acid substitutions, additions and/or deletions may be made to the CDRs or other sequences (e.g variable domains) provided by the present invention without significantly altering the ability of the antibody to bind to TNF. The effect of any amino acid substitutions, additions and/or deletions can be readily tested by one skilled in the art, for example by using the methods described herein, in particular in the Examples, to determine TNF binding/blocking.

In addition one or more (for example 1, 2, 3, 4, 5, 6, 7, 8, 9 or 10) amino acid substitutions, additions and/or deletions may be made to the heavy and/or light chain framework region employed in the antibody or fragment provided by the present invention and wherein binding affinity to TNF is retained or increased.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

Antibodies and fragments of the present disclosure block TNF binding and/or signalling. Blocking as employed herein refers to physically blocking such as occluding the receptor but will also include where the antibody or fragments binds an epitope that causes, for example a conformational change which means that the natural ligand to the receptor no longer binds. Antibody molecules of the present invention bind to TNF and thereby decrease or prevent (e.g. inhibit/neutralise) TNF binding to its target/receptor.

Antibodies for use in the present disclosure may be obtained using any suitable method known in the art. The TNF polypeptide/protein including fusion proteins, cells (recombinantly or naturally) expressing the polypeptide (such as activated T cells) can be used to produce antibodies which specifically recognise TNF. The polypeptide may be the 'mature' polypeptide or a biologically active fragment or derivative thereof.

Polypeptides, for use to immunize a host, may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The TNF polypeptide may in some instances be part of a larger protein such as a fusion protein for example fused to an affinity tag or similar.

Antibodies generated against the TNF polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15):7843-78481; WO92/02551; WO2004/051268 and International Patent Application number WO2004/106377.

Screening for antibodies can be performed using assays to measure binding to human TNF and/or assays to measure the ability to block TNF binding to the receptor. An example of a binding assay is an ELISA. Examples of suitable antagonistic and blocking assays are described in the Examples herein below.

Specific as employed herein is intended to refer to an antibody that only recognises the antigen to which it is specific or an antibody that has significantly higher binding affinity to the antigen to which it is specific compared to binding to antigens to which it is non-specific, for example at least 5, 6, 7, 8, 9, 10 times higher binding affinity. Binding affinity may be measured by techniques such as BIAcore as described herein below.

The amino acid sequences and the polynucleotide sequences of certain antibodies according to the present disclosure are provided and form an aspect of the invention.

Thus in one aspect there is provided an anti-TNF antibody or binding fragment thereof comprising a heavy chain or heavy chain fragment having a variable region, wherein said variable region comprises one, two or three CDRs independently selected from SEQ ID NO: 1, SEQ ID NO: 2 and SEQ ID NO: 3, for example wherein CDR H1 is SEQ ID NO: 1, CDR H2 is SEQ ID NO: 2 and/or CDR H3 is SEQ ID NO: 3.

Thus one embodiment CDR H1 is SEQ ID NO: 1 and CDR H2 is SEQ ID NO: 2, or CDR H1 is SEQ ID NO: 1 and CDR H3 is SEQ ID NO: 3, or CDR H2 is SEQ ID NO: 2 and CDR H3 is SEQ ID NO: 3.

In one embodiment the antibodies or binding fragments according to the present disclosure comprise a light chain or light chain fragment having a variable region, for example comprising one, two or three CDRs independently selected from SEQ ID NO: 4 to 10, in particular wherein CDR L1 has the sequence given in SEQ ID NO: 4 or 5, CDR L2 has the sequence given in SEQ ID NO: 6, 7, 8 or 9 and CDR L3 has the sequence given in SEQ ID NO: 10.

Thus one embodiment CDR L1 is SEQ ID NO: 4 and CDR L2 is SEQ ID NO: 6, 7, 8 or 9 CDR L1 is SEQ ID NO: 5 and CDR L2 is SEQ ID NO: 6, 7, 8 or 9 or CDR L1 is SEQ ID NO: 4 or 5 and CDR L3 is SEQ ID NO: 10; or CDR L2 is SEQ ID NO: 6, 7, 8 or 9 or CDR L1 is SEQ ID NO: 10.

In one embodiment the antibodies or binding fragments according to the present disclosure comprise CDR sequences selected from SEQ ID NOs: 1 to 10, for example wherein CDR H1 is SEQ ID NO: 1, CDR H2 is SEQ ID NO: 2, CDR H3 is SEQ ID NO: 3, CDR L1 is SEQ ID NO: 4 or 5, CDR L2 is SEQ ID NO: 6, 7, 8 or 9 and CDR L3 is SEQ ID NO: 10.

In one embodiment, the antibody of the present invention comprises a heavy chain having 3 heavy chain CDRs and the sequence of CDRH1 has at least 60% identity or similarity to the sequence given in SEQ ID NO: 1, the sequence of CDRH2 has at least 60% identity or similarity to the sequence given in SEQ ID NO: 2 and the sequence of CDRH3 has at least 60% identity or similarity to the sequence given in SEQ ID NO: 3.

In one embodiment, the antibody of the present invention comprises a light chain having three light chain CDRS and the sequence of CDRL1 has at least 60% identity or similarity to the sequence given in SEQ ID NO: 4 or SEQ ID NO: 5, the sequence of CDRL2 has at least 60% identity or similarity to the sequence given in SEQ ID NO: 6, SEQ ID NO: 7, SEQ ID NO: 8 or SEQ ID NO: 9 and the sequence of CDRL3 has at least 60% identity or similarity to the sequence given in SEQ ID NO: 10.

In one embodiment the antibodies or binding fragments according to the present disclosure are fully human, for example prepared from a phage library or similar.

In one embodiment the antibody or fragments according to the disclosure are humanised.

Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived. The latter are often referred to as donor residues.

Thus in one embodiment as used herein, the term 'humanised antibody molecule' refers to an antibody molecule wherein the heavy and/or light chain contains one or more CDRs (including, if desired, one or more modified CDRs) from a donor antibody (e.g. a non-human antibody such as a murine monoclonal antibody) grafted into a heavy and/or light chain variable region framework of an acceptor antibody (e.g. a human antibody) optionally further comprising one or more framework residues derived from the non-human species from which the CDRs were derived (donor residues). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions.

Suitably, the humanised antibody according to the present invention has a variable domain comprising human acceptor framework regions as well as one or more of the CDRs provided specifically herein. Thus, provided in one embodiment is blocking humanised antibody which binds human TNF wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at www.imgt.org.

In a humanised antibody of the present invention, the acceptor heavy and light chains do not necessarily need to be derived from the same antibody and may, if desired, comprise composite chains having framework regions derived from different chains.

One such suitable framework region for the heavy chain of the humanised antibody of the present invention is derived from the human VK1 2-1(U) A20 JK2 or VH3 1-3 3-21 JH4 acceptor framework (SEQ ID NO: 25 and 26 respectively).

Accordingly, in one example there is provided a humanised antibody comprising one or more CDRs selected from the sequence given in SEQ ID NO: 1 for CDR-H1, the sequence given in SEQ ID NO: 2 for CDR-H2 and the sequence given in SEQ ID NO: 3 for CDRH3, wherein the heavy chain framework region is derived from the human acceptor framework VH3 1-3 3-21 JH4 (SEQ ID NO: 26).

Accordingly, in one example there is provided a humanised antibody comprising the sequence given in SEQ ID NO: 1 for CDR-H1, the sequence given in SEQ ID NO: 2 for CDR-H 2 and the sequence given in SEQ ID NO: 3 for CDRH3, wherein the heavy chain framework region is derived from the human acceptor framework VH3 1-3 3-21 JH4 (SEQ ID NO: 26).

In one example the heavy chain variable domain of the antibody comprises the sequence given in SEQ ID NO: 12, 16 or 28, such as 12 or 16.

A suitable framework region for the light chain of the humanised antibody of the present invention is derived from the human acceptor framework VK1 2-1(U) A20 JK2 (SEQ ID NO: 25).

Accordingly, in one example there is provided a humanised antibody comprising the sequence given in SEQ ID NO: 4 or 5 for CDR-L1, the sequence given in SEQ ID NO: 6, 7, 8 or 9 for CDR-L2 and the sequence given in SEQ ID NO: 10 for CDRL3, wherein the light chain framework region is derived from the human acceptor framework VK1 2-1(U) A20 JK2.

In one example the light chain variable domain of the antibody comprises the sequence given in SEQ ID NO: 11, 15 or 27, such as 11 or 15. In one example the light chain variable domain of the antibody comprises the sequence given in SEQ ID NO: 29.

In one embodiment the antibody or binding fragment comprises a heavy chain variable region of SEQ ID NO: 12 and a light chain variable region sequence of SEQ ID NO: 11.

In one embodiment the antibody or binding fragment comprises a heavy chain variable region of SEQ ID NO: 12 and a light chain variable region sequence of SEQ ID NO: 29.

In one embodiment the antibody or binding fragment comprises a heavy chain variable region of SEQ ID NO: 16 and a light chain variable region sequence of SEQ ID NO: 15.

In one embodiment the antibody or binding fragment comprises a heavy chain variable region of SEQ ID NO: 28 and a light chain variable region sequence of SEQ ID NO: 27.

In a humanised antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO91/09967.

Thus in one embodiment 1, 2, 3, 4, 5, 6, 7, 8, 9 or 10 residues in the heavy and/or light chain framework are replaced with an alternative amino acid residue.

Accordingly, in one example there is provided a humanised antibody, wherein at least one of the residues at positions 24, 48, 49 71, 73, 78 and 93 of the variable domain of the heavy chain (Kabat numbering) are donor residues, see for example the sequence given in SEQ ID NO: 12 or SEQ ID NO: 28.

In one embodiment residue 24 of the heavy chain variable domain is replaced with an alternative amino acid, for example threonine.

In one embodiment residue 48 of the heavy chain variable domain is replaced with an alternative amino acid, for example isoleucine.

In one embodiment residue 49 of the heavy chain variable domain is replaced with an alternative amino acid, for example glycine.

In one embodiment residue 71 of the heavy chain variable domain is replaced with an alternative amino acid, for example valine.

In one embodiment residue 73 of the heavy chain variable domain is replaced with an alternative amino acid, for example lysine.

In one embodiment residue 78 of the heavy chain variable domain is replaced with an alternative amino acid, for example alanine.

In one embodiment residue 93 of the heavy chain variable domain is replaced with an alternative amino acid, for example threonine.

In one embodiment residue 48 is isoleucine, residue 49 is glycine, 71 is valine, 73 is lysine, 78 is alanine and residue 93 is threonine in the humanised heavy chain variable region according to the present disclosure.

Accordingly, in one example there is provided a humanised antibody, wherein at least the residues at each of positions 48, 49 71, 73, 78 and 93 of the variable domain of the heavy chain (Kabat numbering) are donor residues, see for example the sequence given in SEQ ID NO: 12.

In one example there is provided a humanised antibody, wherein at least the residues at each of positions 24, 48, 49 71, 73, 78 and 93 of the variable domain of the heavy chain (Kabat numbering) are donor residues, see for example the sequence given in SEQ ID NO: 28.

In one example there is provided a humanised antibody, wherein one or more of the residues at positions 65, 71 and 87 of the variable domain of the light chain (Kabat numbering) are donor residues, see for example the sequence given in SEQ ID NO: 11 or SEQ ID NO: 27.

In one example there is provided a humanised antibody, wherein at least the residues at each of positions 65, 71 and 87 of the variable domain of the light chain (Kabat numbering) are donor residues, see for example the sequence given in SEQ ID NO: 11.

In one embodiment residue 65 of the light chain variable domain is replaced with an alternative amino acid, for example threonine.

In one embodiment residue 71 of the light chain variable domain is replaced with an alternative amino acid, for example tyrosine.

In one embodiment residue 87 of the light chain variable domain is replaced with an alternative amino acid, for example phenylalanine.

In one embodiment residue 65 is threonine, residue 71 is tyrosine and residue 87 is phenylalanine in the humanised light chain variable region according to the present disclosure.

In one embodiment, the present invention provides an antibody molecule which binds human TNF comprising a heavy chain, wherein the variable domain of the heavy chain comprises a sequence having at least 80%, 85%, 90%, 91%, 92%, 93%, 94%, 95% 96%, 97%, 98% or 99% identity or similarity to a sequence herein, for example the sequence given in SEQ ID NO: 12, 16 or 28.

In one embodiment, the present invention provides an antibody molecule which binds human TNF comprising a light chain, wherein the variable domain of the light chain comprises a sequence having at least 80%, 85%, 90%, 91%, 92%, 93%, 94%, 95% 96%, 97%, 98% or 99% identity or similarity to the sequence given in SEQ ID NO: 11, 15 or 27.

In one embodiment the present invention provides an antibody molecule which binds human TNF wherein the antibody has a heavy chain variable domain which is at least 90%, 91%, 92%, 93%, 94%, 95% 96%, 97%, 98% or 99% similar or identical to a sequence given herein, for example the sequence given in SEQ ID NO: 12, 15 OR 28 but wherein the antibody molecule has the sequence given in SEQ ID NO: 1 for CDR-H1, the sequence given in SEQ ID NO: 2 for CDR-H2 and the sequence given in SEQ ID NO: 3 for CDR-H3.

In one embodiment the present invention provides an antibody molecule which binds human TNF wherein the antibody has a light chain variable domain which is at least 90%, 91%, 92%, 93%, 94%, 95% 96%, 97%, 98% or 99% similar or identical to a sequence given herein, for example the sequence in SEQ ID NO: 11, 15 or 27 but wherein the antibody molecule has the sequence given in SEQ ID NO: 4 or 5 for CDR-L1, the sequence given in SEQ ID NO: 6, 7, 8 or 9 for CDR-L2 and the sequence given in SEQ ID NO: 10 for CDR-L3.

In one embodiment the present invention provides an antibody molecule which binds human TNF wherein the antibody has a heavy chain variable domain which is at least 90%, 91%, 92%, 93%, 94%, 95% 96%, 97%, 98% or 99% similar or identical to a sequence given herein, for example the sequence given in SEQ ID NO: 12 and a light chain variable domain which is at least 90%, 91%, 92%, 93%, 94%, 95% 96%, 97%, 98% or 99% similar or identical to a sequence given herein, for example the sequence given in SEQ ID NO: 11 but wherein the antibody molecule has the sequence given in SEQ ID NO: 1 for CDR-H1, the sequence given in SEQ ID NO: 2 for CDR-H2, the sequence given in SEQ ID NO: 3 for CDR-H3, the sequence given in SEQ ID NO: 4 or 5 for CDR-L1, the sequence given in SEQ ID NO: 6, 7, 8 or 9 for CDR-L2 and the sequence given in SEQ ID NO: 10 for CDR-L3.

In one embodiment the present invention provides an antibody molecule which binds human TNF wherein the antibody has a heavy chain variable domain which is at least 90%, 91%, 92%, 93%, 94%, 95% 96%, 97%, 98% or 99% similar or identical to a sequence given herein, for example the sequence given in SEQ ID NO: 16 and a light chain variable domain which is at least 90%, 91%, 92%, 93%, 94%, 95% 96%, 97%, 98% or 99% similar or identical to a sequence given herein, for example the sequence given in SEQ ID NO: 15 but wherein the antibody molecule has the sequence given in SEQ ID NO: 1 for CDR-H1, the sequence given in SEQ ID NO: 2 for CDR-H2, the sequence given in SEQ ID NO: 3 for CDR-H3, the sequence given in SEQ ID NO: 4 or 5 for CDR-L1, the sequence given in SEQ ID NO: 6, 7, 8 or 9 for CDR-L2 and the sequence given in SEQ ID NO: 10 for CDR-L3.

In one embodiment the present invention provides an antibody molecule which binds human TNF wherein the antibody has a heavy chain variable domain which is at least 90%, 91%, 92%, 93%, 94%, 95% 96%, 97%, 98% or 99% similar or identical to a sequence given herein, for example the sequence given in SEQ ID NO: 28 and a light chain variable domain which is at least 90%, 91%, 92%, 93%, 94%, 95% 96%, 97%, 98% or 99% similar or identical to a sequence given herein, for example the sequence given in SEQ ID NO: 27 but wherein the antibody molecule has the sequence given in SEQ ID NO: 1 for CDR-H1, the sequence given in SEQ ID NO: 2 for CDR-H2, the sequence given in SEQ ID NO: 3 for CDR-H3, the sequence given in SEQ ID NO: 4 or 5 for CDR-L1, the sequence given in SEQ ID NO: 6, 7, 8 or 9 for CDR-L2 and the sequence given in SEQ ID NO: 10 for CDR-L3.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

The antibody molecules of the present invention may comprise a complete antibody molecule having full length heavy and light chains or a fragment thereof and may be, but are not limited to Fab, modified Fab, Fab', modified Fab', F(ab')$_2$, Fv, single domain antibodies (e.g. VH or VL or VHH), scFv, dsscFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities e.g bispecific or may be monospecific (see for example WO 92/22853, WO05/113605, WO2009/040562 and WO2010/035012).

In one example the present invention provides a multi-specific antibody comprising any one of the anti-TNF antibodies or binding fragments thereof described herein. The multispecific antibody may have any suitable antibody format which is capable of binding two or more antigens. Examples of multi-specific antibody formats are known in the art and may include for example and may be selected from diabody, scdiabody, triabody, tandem scFv, FabFv, Fab'Fv, FabdsFv, Fab-scFv, Fab-dsscFv, Fab-(dsscFv)2, FabFvFv, FabFvFc, diFab, diFab', tribody, tandem scFv-Fc, scFv-Fc-scFv, scdiabody-Fc, scdiabody-CH3, Ig-scFv, scFv-Ig, V-Ig, Ig-V, Duobody and DVD-Ig. In one example the multi-specific antibody is a disulphide stabilised antibody as described in WO2015/197772.

In one aspect of the present invention, a multi-specific antibody molecule is provided as a dimer comprising or consisting of:

a) a polypeptide chain of formula (I):

$V_{H1}$-$CH_1$-X-$V_1$; and b) a polypeptide chain of formula (II):

$V_{L1}$-$C_L$-Y-$V_2$;

wherein:
$V_H1$ represents a heavy chain variable domain;
$CH_1$ represents a domain of a heavy chain constant region, for example domain 1 thereof;
X represents a bond or linker;
Y represents a bond or linker;
V1 represents a dsFv, a sdAb, a scFv or a dsscFv;
$V_{L1}$ represents a light chain variable domain;
$C_L$ represents a domain from a light chain constant region, such as Ckappa;
V2 represents dsFv, a sdAb, a scFv or a dsscFv
wherein $V_{H1}$ and $V_{LA}$ together form a binding domain specific to a first antigen and V1 and V2 each bind a second and third antigen respectively and wherein at least one of the antigens is TNF.

In one example the antibody molecule is a scFv comprising the sequence given in SEQ ID NO: 21.

In one example the antibody molecule comprises one or more scFv molecules comprising the sequences given in SEQ ID NO: 11 and 12, SEQ ID NO: 15 and 16 and/or the sequence given in SEQ ID NO: 21.

In one embodiment the antibody molecule of the present disclosure is an antibody Fab or Fab' fragment comprising the variable regions shown in SEQ ID NOs: 11 and 12, for example for the light and heavy chain respectively.

In one embodiment the antibody molecule of the present disclosure is an antibody Fab or Fab' fragment comprising the variable regions shown in SEQ ID NOs: 15 and 16, for example for the light and heavy chain respectively.

In one embodiment the antibody molecule of the present disclosure is an antibody Fab or Fab' fragment comprising the variable regions shown in SEQ ID NOs: 27 and 28, for example for the light and heavy chain respectively.

It will be appreciated that the scFv and Fab molecules of the disclosure may be incorporated into any suitable multi-specific antibody molecule as described herein above, for example the multi-specific antibody molecule having the formula I and II above.

In one embodiment the antibody molecule of the present disclosure is a full length IgG1 antibody comprising the variable regions shown in SEQ ID NOs: 11 and 12, for example for the light and heavy chain respectively.

In one embodiment the antibody molecule of the present disclosure is a full length IgG1 antibody comprising the variable regions shown in SEQ ID NOs: 15 and 16, for example for the light and heavy chain respectively.

In one embodiment the antibody molecule of the present disclosure is a full length IgG1 antibody comprising the variable regions shown in SEQ ID NOs: 27 and 28, for example for the light and heavy chain respectively.

In one embodiment the antibody molecule of the present disclosure is a full length IgG4 format. In one embodiment the antibody molecule of the present disclosure is a full length IgG4P format.

In one embodiment the antibody molecule of the present disclosure is a full length IgG4 or IgG4P antibody comprising the variable regions shown in SEQ ID NOs: 11 and 12, for example for the light and heavy chain respectively.

IgG4P as employed herein is a mutation of the wild-type IgG4 isotype where amino acid 241 is replaced by proline, see for example where serine at position 241 has been changed to proline as described in Angal et al., Molecular Immunology, 1993, 30 (1), 105-108.

In one embodiment the antibody according to the present disclosure is provided as an TNF binding antibody fusion protein which comprises an immunoglobulin moiety, for example a Fab or Fab' fragment, and one or two single domain antibodies (dAb) linked directly or indirectly thereto, for example as described in WO2009/040562, WO2010035012, WO2011/030107, WO2011/061492 and WO2011/086091 all incorporated herein by reference.

In one embodiment the fusion protein comprises two domain antibodies, for example as a variable heavy (VH) and variable light (VL) pairing, optionally linked by a disulphide bond.

In one embodiment the Fab or Fab' element of the fusion protein has the same or similar specificity to the single domain antibody or antibodies. In one embodiment the Fab or Fab' has a different specificity to the single domain antibody or antibodies, that is to say the fusion protein is multivalent. In one embodiment a multivalent fusion protein according to the present invention has an albumin binding site, for example a VH/VL pair therein provides an albumin binding site.

In one embodiment the Fab or Fab' according to the present disclosure is conjugated to a PEG molecule or human serum albumin.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705: 129-134, 1995). Accordingly, the C-terminal lysine of the antibody heavy chain may be absent.

In one embodiment the antibody heavy chain comprises a CH1 domain, for example the CH1 sequence shown in SEQ ID NO: 34, and the antibody light chain comprises a CL domain, either kappa or lambda, for example the CL sequence shown in SEQ ID NO: 33.

In one embodiment the antibody heavy chain comprises a full length constant region comprising CH1, CH2 and CH3 domains, for example the gamma 1 constant region sequence shown in SEQ ID NO: 35 or the gamma 4 constant region sequence shown in SEQ ID NO: 36 or SEQ ID NO: 37 and the antibody light chain comprises a CL domain, either kappa or lambda, for example the CL sequence shown in SEQ ID NO: 33.

In one embodiment a C-terminal amino acid from the antibody molecule is cleaved during post-translation modifications.

In one embodiment an N-terminal amino acid from the antibody molecule is cleaved during post-translation modifications.

Also provided by the present invention is a specific region or epitope of human TNF which is bound by an antibody provided by the present invention, in particular an antibody or binding fragment comprising:
the heavy chain sequence of SEQ ID NO: 12 and the light chain sequence of SEQ ID NO: 11,
the heavy chain sequence of SEQ ID NO: 16 and the light chain sequence of SEQ ID NO: 15, or
the heavy chain sequence of SEQ ID NO: 28 and the light chain sequence of SEQ ID NO: 27.

This specific region or epitope of the human TNF polypeptide can be identified by any suitable epitope mapping method known in the art in combination with any one of the antibodies provided by the present invention. Examples of such methods include screening peptides of varying lengths derived from TNF for binding to the antibody of the present invention with the smallest fragment that can specifically bind to the antibody containing the sequence of the epitope recognised by the antibody. The TNF peptides may be produced synthetically or by proteolytic digestion of the TNF polypeptide. Peptides that bind the antibody can be identified by, for example, mass spectrometric analysis. In another example, NMR spectroscopy or X-ray crystallography can be used to identify the epitope bound by an antibody of the present invention. In one example where X-ray crystallography is used, the epitope is determined as those residues on the TNF polypeptide which are within 4 Å of the antibody. In one example the epitope is determined as those residues on the TNF polypeptide which are within 5 Å of the antibody. Once identified, the epitopic fragment which binds an antibody of the present invention can be used, if required, as an immunogen to obtain additional antibodies which bind the same epitope.

In one embodiment the antibodies which bind the epitope described herein above provided by the present invention are fully human. In one embodiment they are humanised. In one example they have an affinity for human TNF of 150 pM or less, typically 130 pM or less.

Antibodies which cross-block the binding of an antibody molecule according to the present invention in particular, an antibody molecule comprising:
the heavy chain sequence given in SEQ ID NO: 12 and the light chain sequence given in SEQ ID NO: 11,
the heavy chain sequence given in SEQ ID NO: 16 and the light chain sequence given in SEQ ID NO: 15, or
the heavy chain sequence given in SEQ ID NO: 28 and the light chain sequence given in SEQ ID NO: 27
may be similarly useful in blocking TNF activity. Accordingly, the present invention also provides an anti-TNF antibody molecule, which cross-blocks the binding of any one of the antibody molecules described herein above to human TNF and/or is cross-blocked from binding human TNF by any one of those antibodies. In one embodiment, such an antibody binds to the same epitope as an antibody described herein above. In another embodiment the cross-blocking neutralising antibody binds to an epitope which borders and/or overlaps with the epitope bound by an antibody described herein above.

Cross-blocking antibodies can be identified using any suitable method in the art, for example by using competition ELISA or BIAcore assays where binding of the cross blocking antibody to human TNF prevents the binding of an antibody of the present invention or vice versa. Such cross blocking assays may use isolated natural or recombinant TNF or a suitable fusion protein/polypeptide. In one example binding and cross-blocking is measured using recombinant human TNF.

In one embodiment the cross-blocking antibodies provided by the present invention inhibit the binding of an antibody comprising:
the heavy chain sequence given in SEQ ID NO: 12 and the light chain sequence given in SEQ ID NO: 11,
the heavy chain sequence given in SEQ ID NO: 16 and the light chain sequence given in SEQ ID NO: 15, or
the heavy chain sequence given in SEQ ID NO: 28 and the light chain sequence given in SEQ ID NO: 27
by greater than 80%, for example by greater than 85%, such as by greater than 90%, in particular by greater than 95% inhibition.

In one embodiment the cross-blocking antibodies provided by the present invention are fully human. In one embodiment the cross-blocking antibodies provided by the present invention are humanised. In one embodiment the cross-blocking antibodies provided by the present invention have an affinity for human TNF of 150 pM or less, 130 pM or less or 100 pM or less. In one embodiment the cross-blocking antibodies provided by the present invention have an affinity for human TNF of 50 pM or less. Affinity can be measured using the methods described herein below.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent accessible surface thereof carries no net electrical charge. In one example, the TNF antibody and fragments of the invention may be engineered to have an appropriate isoelectric point. This may lead to antibodies and/or fragments with more robust properties, in particular suitable solubility and/or stability profiles and/or improved purification characteristics.

Thus in one aspect the invention provides a humanised TNF antibody engineered to have an isoelectric point different to that of the originally identified antibody. The antibody may, for example be engineered by replacing an amino acid residue such as replacing an acidic amino acid residue with one or more basic amino acid residues. Alternatively, basic amino acid residues may be introduced or acidic amino acid residues can be removed. Alternatively, if the molecule has an unacceptably high pI value acidic residues may be introduced to lower the pI, as required. It is important that when manipulating the pI care must be taken to retain the desirable activity of the antibody or fragment. Thus in one embodiment the engineered antibody or fragment has the same or substantially the same activity as the "unmodified" antibody or fragment.

Programs such as ** ExPASY www.expasy.ch/tools/pi_tool.html, and www.iut-arles.up.univ-mrs.fr/w3bb/d_abim/compo-p.html, may be used to predict the isoelectric point of the antibody or fragment. Alternatively or additionally, the pI can be measured using any suitable standard laboratory technique.

The antibody molecules of the present invention suitably have a high binding affinity, in particular in the nanomolar range. Affinity may be measured using any suitable method known in the art, including BIAcore, as described in the Examples herein, using isolated natural or recombinant TNF or a suitable fusion protein/polypeptide. In one example affinity is measured using recombinant human TNF.

Suitably the antibody molecules of the present invention have a binding affinity for isolated human TNF of about 1 nM or lower. In one embodiment the antibody molecule of the present invention has a binding affinity of about 500 pM or lower (i.e. higher affinity). In one embodiment the antibody molecule of the present invention has a binding affinity of about 250 pM or lower. In one embodiment the antibody molecule of the present invention has a binding affinity of about 200 pM or lower. In one embodiment the antibody molecule of the present invention has a binding affinity of about 150 pM or lower. In one embodiment the present invention provides an anti-TNF antibody with a binding affinity of about 100 pM or lower. In one embodiment the present invention provides a humanised anti-TNF antibody with a binding affinity of about 100 pM or lower. In one embodiment the present invention provides an anti-TNF antibody with a binding affinity of 50 pM or lower.

The affinity of an antibody or binding fragment of the present invention, as well as the extent to which a binding agent (such as an antibody) inhibits binding, can be determined by one of ordinary skill in the art using conventional techniques, for example those described by Scatchard et al. (Ann. K Y. Acad. Sci. 51:660-672 (1949)) or by surface plasmon resonance (SPR) using systems such as BIAcore. For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al, Cancer Res. 53:2560-65 (1993)).

It will be appreciated that the affinity of antibodies provided by the present invention may be altered using any suitable method known in the art. The present invention therefore also relates to variants of the antibody molecules of the present invention, which have an improved affinity for TNF. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment the antibody molecules of the present invention block human TNF activity. Assays suitable for determining the ability of an antibody to block TNF are known in the art.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, $Lu^{177}$, $Bismuth^{213}$, $Californium^{252}$, $Iridium^{192}$ and $Tungsten^{188}$/$Rhenium^{188}$; or drugs such as but not limited to, alkylphosphocholines, topoisomerase I inhibitors, taxoids and suramin. Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

In one embodiment the polymer is albumin or a fragment thereof, such as human serum albumin or a fragment thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment, Fab' fragment or diFab which is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA3 (wherein m in the structure below is 5) and GL2-400MA (where m is 2) and n is approximately 450:

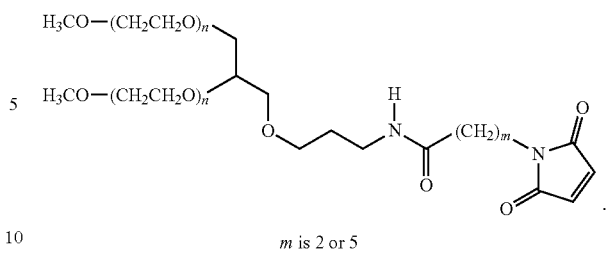

m is 2 or 5

That is to say each PEG is about 20,000 Da.

Thus in one embodiment the PEG is 2,3-Bis(methylpolyoxyethylene-oxy)-1-{[3-(6-maleimido-1 1-oxohexyl) amino]propyloxy} hexane (the 2 arm branched PEG, —CH$_2$)$_3$NHCO(CH$_2$)$_5$-MAL, Mw 40,000 known as SUNBRIGHT GL2-400MA3.

Further alternative PEG effector molecules of the following type:

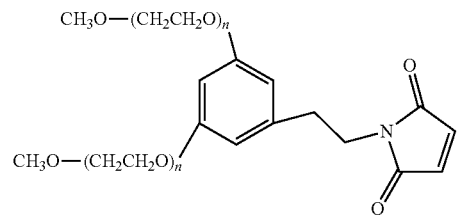

are available from Dr Reddy, NOF and Jenkem.

In one embodiment there is provided an antibody which is PEGylated (for example with a PEG described herein), attached through a cysteine amino acid residue at or about amino acid 232 in the chain, for example amino acid 232 of the heavy chain (by sequential numbering).

In one embodiment the present disclosure provides a Fab' PEG molecule comprising one or more PEG polymers, for example 1 or 2 polymers such as a 40 kDa polymer or polymers.

Fab'-PEG molecules according to the present disclosure may be particularly advantageous in that they have a half-life independent of the Fc fragment. In one example the present invention provides a method treating a disease ameliorated by blocking human TNF comprising administering a therapeutically effective amount of an anti-TNF antibody or binding fragment thereof wherein the antibody or binding fragment thereof has a half life that is independent of Fc binding to TNF.

In one embodiment there is provided a Fab' conjugated to a polymer, such as a PEG molecule, a starch molecule or an albumin molecule.

In one embodiment there is provided a scFv conjugated to a polymer, such as a PEG molecule, a starch molecule or an albumin molecule.

In one embodiment the antibody or fragment is conjugated to a starch molecule, for example to increase the half life. Methods of conjugating starch to a protein as described in U.S. Pat. No. 8,017,739 incorporated herein by reference.

The present invention also provides an isolated DNA sequence encoding the heavy and/or light chain(s) of an antibody molecule of the present invention. Suitably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable DNA sequences are provided in herein.

Examples of suitable DNA sequences encoding the 2109 gL18 light chain variable region are provided in SEQ ID NO: 13 and SEQ ID NO: 17.

Examples of suitable DNA sequences encoding the 2109 gH2 heavy chain variable region are provided in SEQ ID NO: 14 and SEQ ID NO: 18.

Accordingly in one example the present invention provides an isolated DNA sequence encoding the heavy chain of an antibody Fab or Fab' fragment of the present invention which comprises the sequence given in SEQ ID NO: 13, 17, 14 or 18 (such as 13 and 14 or 17 and 18).

In one example the present invention provides an isolated DNA sequence encoding the heavy chain and the light chain of an IgG4(P) antibody of the present invention in which the DNA encoding the heavy chain comprises the sequence given in SEQ ID NO: 13 or 17 and the DNA encoding the light chain comprises the sequence given in SEQ ID NO: 14 or 18.

In one example the present invention provides an isolated DNA sequence encoding the heavy chain and the light chain of an IgG1 antibody of the present invention in which the DNA encoding the heavy chain comprises the sequence given in SEQ ID NO: 13 or 17 and the DNA encoding the light chain comprises the sequence given in SEQ ID NO: 14 or 18.

In one example the present invention provides an isolated DNA sequence encoding the heavy chain and the light chain of a Fab-dsFv antibody of the present invention in which the DNA encoding the heavy chain comprises the sequence given in SEQ ID NO: 13 or 17 and the DNA encoding the light chain comprises the sequence given in SEQ ID NO: 14 or 18.

The present invention also relates to a cloning or expression vector comprising one or more DNA sequences of the present invention. Accordingly, provided is a cloning or expression vector comprising one or more DNA sequences encoding an antibody of the present invention. Suitably, the cloning or expression vector comprises two DNA sequences, encoding the light chain and the heavy chain of the antibody molecule of the present invention, respectively and suitable signal sequences. In one example the vector comprises an intergenic sequence between the heavy and the light chains (see WO03/048208).

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Accordingly the present invention also provides a host cell for expression of an antibody according to to the invention comprising:

i) a DNA sequence encoding the heavy chain of said antibody, and ii) a DNA sequence encoding the light chain of said antibody wherein the DNA sequences are provided in one or more cloning or expression vectors.

Any suitable host cell/vector system may be used for expression of the DNA sequences encoding the antibody molecule of the present invention. Bacterial, for example *E. coli*, and other microbial systems may be used (especially for expressing antibody fragments or eukaryotic, for example mammalian, host cell expression systems may also be used (especially for expressing full-length antibodies). Suitable mammalian host cells include CHO, myeloma or hybridoma cells.

Suitable types of Chinese Hamster Ovary (CHO cells) for use in the present invention may include CHO and CHO-K1 cells including dhfr-CHO cells, such as CHO-DG44 cells and CHO-DXB 11 cells, which may be used with a DHFR selectable marker or CHOK1-SV cells which may be used with a glutamine synthetase selectable marker. Other cell types of use in expressing antibodies include lymphocytic cell lines, e.g., NS0 myeloma cells and SP2 cells, COS cells.

The present invention also provides a process for the production of an antibody molecule according to the present invention comprising culturing a host cell containing a vector or vectors of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibodies and fragments according to the present disclosure are expressed at good levels from host cells. Thus the properties of the antibodies and/or fragments are conducive to commercial processing.

Thus there is a provided a process for culturing a host cell and expressing an antibody or fragment thereof, isolating the latter and optionally purifying the same to provide an isolated antibody or fragment. In one embodiment the process further comprises the step of conjugating an effector molecule to the isolated antibody or fragment, for example conjugating to a PEG polymer in particular as described herein.

In one embodiment there is provided a process for purifying an antibody (in particular an antibody or fragment according to the invention) comprising the steps: performing anion exchange chromatography in non-binding mode such that the impurities are retained on the column and the antibody is eluted.

Thus the chromatograph step or steps may include one or more washing steps, as appropriate.

The purification process may also comprise one or more filtration steps, such as a diafiltration step.

Thus in one embodiment there is provided a purified anti-TNF antibody or fragment, for example a humanised antibody or fragment, in particular an antibody or fragment according to the invention, in substantially purified from, in particular free or substantially free of endotoxin and/or host cell protein or DNA.

Purified form as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 µg per mg of antibody product or less such as 100 µg per mg or less, in particular 20 µg per mg, as appropriate.

The antibody molecules of the present invention may also be used in diagnosis, for example in the in vivo diagnosis and imaging of disease states involving TNF.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody molecule of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable excipient.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients or non-antibody ingredients such as steroids or other drug molecules, in particular drug molecules whose half-life is independent of TNF binding.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 500 mg/kg, for example 0.1 mg/kg to 200 mg/kg, such as 100 mg/Kg.

Pharmaceutical compositions may be conveniently presented in unit dose forms containing a predetermined amount of an active agent of the invention per dose.

Therapeutic doses of the antibodies according to the present disclosure show no apparent toxicology effects in vivo.

Compositions may be administered individually to a patient or may be administered in combination (e.g. simultaneously, sequentially or separately) with other agents, drugs or hormones.

Agents as employed herein refers to an entity which when administered has a physiological affect.

Drug as employed herein refers to a chemical entity which at a therapeutic dose has an appropriate physiological affect.

In one embodiment the antibodies or fragments according to the present disclosure are employed with an immunosuppressant therapy, such as a steroid, in particular prednisone.

In one embodiment the antibodies or fragments according to the present disclosure are employed with Rituximab or other B cell therapies.

In one embodiment the antibodies or fragments according to the present disclosure are employed with any B cell or T cell modulating agent or immunomodulator. Examples include methotrexate, microphenyolate and azathioprine.

The dose at which the antibody molecule of the present invention is administered depends on the nature of the condition to be treated, the extent of the inflammation present and on whether the antibody molecule is being used prophylactically or to treat an existing condition.

The frequency of dosing will depend on the half life of the antibody, its target-mediated disposition, the duration of its effect, and the presence of anti-drug antibodies. If the antibody has a short half life (a few hours) or a limited activity, and/or if it is desirable to deliver small volumes of drug (e.g. for subcutaneous injection), it may be necessary to dose frequently, as frequently as once or more per day. Alternatively, if the antibody has a long half life, has long duration of activity, or can be dosed in large volumes (such as by infusion) dosing may be infrequent, once per day, or every few days, weeks or months. In one embodiment, sufficient time is allowed between doses to allow anti-drug antibody levels to decline.

Half life as employed herein is intended to refer to the duration of the molecule in circulation, for example in serum/plasma.

Pharmacodynamics as employed herein refers to the profile and in particular duration of the biological action of the molecule according the present disclosure.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody or fragment, for example if the pI of the protein is in the range 8-9 or above then a formulation pH of 7 may be appropriate. Whilst not wishing to be bound by theory it is thought that this may ultimately provide a final formulation with improved stability, for example the antibody or fragment remains in solution.

In one example the pharmaceutical formulation at a pH in the range of 4.0 to 7.0 comprises: 1 to 200 mg/mL of an antibody molecule according to the present disclosure, 1 to 100 mM of a buffer, 0.001 to 1% of a surfactant, a) 10 to 500 mM of a stabiliser, b) 10 to 500 mM of a stabiliser and 5 to 500 mM of a tonicity agent, or c) 5 to 500 mM of a tonicity agent.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 1 to 5 μm. The particle size of the active ingredient (such as the antibody or fragment) is of primary importance.

The propellant gases which can be used to prepare the inhalable aerosols are known in the art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellant gases may be used on their own or in mixtures thereof.

Particularly suitable propellant gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus(R) nebulizer connected to a Pari Master(R) compressor manufactured by Pari Respiratory Equipment, Inc., Richmond, Va.).

The antibody of the invention can be delivered dispersed in a solvent, e.g., in the form of a solution or a suspension. It can be suspended in an appropriate physiological solution, e.g., saline or other pharmacologically acceptable solvent or a buffered solution. Examples of buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solutionbuffer.

The antibodies disclosed herein may be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

TNFα is the archetypal member of the TNF superfamily. TNFα is a pleiotropic cytokine that mediates immune regulation and inflammatory responses. In vivo, TNFα is also known to be involved in responses to bacterial, parasitic and viral infections. In particular, TNFα is known to have a role in rheumatoid arthritis (RA), inflammatory bowel diseases (including Crohn's disease), psoriasis, Alzheimer's disease (AD), Parkinson's disease (PD), pain, epilepsy, osteoporosis, asthma, sepsis, fever, Systemic lupus erythematosus (SLE) and Multiple Sclerosis (MS) and cancer. TNFα is also known to have a role in Amyotrophic Lateral Sclerosis (ALS), ischemic stroke, immune complex-mediated glomerulonephritis, lupus nephritis (LN), antineutrophil cytoplasmic antibodies (ANCA-)associated glomerulonephritis, minimal change disease, diabetic nephropathy (DN), acute kidney injury (AKI), obstructive uropathy, kidney allograft rejection, cisplatin-induced AKI and obstructive uropathy.

Accordingly an antibody or composition of the present invention may be used (directly or indirectly) to treat, prevent or ameliorate any condition that that can be treated, prevented or ameliorated by other TNFα antagonists.

The antibodies and compositions of the present invention are accordingly beneficial in the treatment and/or prevention of various human ailments. These include autoimmune and inflammatory disorders; neurological and neurodegenerative disorders; pain and nociceptive disorders; and cardiovascular disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, vasculitis, polymyositis, scleroderma, multiple sclerosis, ankylosing spondylitis, rheumatoid arthritis and Sjögren's syndrome. Autoimmune endocrine disorders include thyroiditis. Organ-specific autoimmune disorders include Addison's disease, haemolytic or pernicious anaemia, glomerulonephritis (including Goodpasture's syndrome), Graves' disease, idiopathic thrombocytopenic purpura, insulin-dependent diabetes mellitus, juvenile diabetes, uveitis, inflammatory bowel disease (including Crohn's disease and ulcerative colitis), pemphigus, atopic dermatitis, autoimmune hepatitis, primary biliary cirrhosis, autoimmune pneumonitis, autoimmune carditis, myasthenia gravis, spontaneous infertility, osteoporosis, asthma and muscular dystrophy (including Duchenne muscular dystrophy).

Neurological and neurodegenerative disorders include Alzheimer's disease, Parkinson's disease, Huntington's disease, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction).

In particular, an antibody of compositions of the present invention may be used to treat or prevent inflammatory disorders, CNS disorders, immune disorders and autoimmune diseases, pain, osteoporosis, fever and organ transplant rejection. In a preferred embodiment, an antibody or composition of the present invention may be used to treat or prevent rheumatoid arthritis, inflammatory bowel diseases (including Crohn's disease), psoriasis, Alzheimer's disease, Parkinson's disease, epilepsy, asthma, sepsis, systemic lupus erythematosus, multiple sclerosis, asthma, rhinitis, cancer and osteoporosis. In another preferred embodiment, an antibody or composition of the present invention may be used to treat or prevent rheumatoid arthritis (RA), non specific inflammatory arthritis, erosive bone disease, chondritis, cartilage degeneration and/or destruction, juvenile inflammatory arthritis, Still's Disease (juvenile and/or adult onset), juvenile idiopathic arthritis, juvenile idiopathic arthritis (both oligoarticular and polyarticular forms), inflammatory bowel diseases (including Crohn's disease, ulcerative colitis, indeterminate colitis, pouchitis), psoriasis, psoriatic arthopathy, ankylosing spondylitis, Sjogren's Disease, Alzheimer's disease (AD), Behcet's Disease, Parkinson's disease (PD), amyotrophic lateral sclerosis (ALS), ischemic stroke, pain, epilepsy, osteoporosis, osteopenia, anaemia of chronic disease, cachexia, diabetes, dyslipidemia, metabolic syndrome, asthma, chronic obstructive airways (or pulmonary) disease, sepsis, fever, respiratory distress syndrome, systemic lupus erythematosus (SLE), multiple sclerosis (MS) immune complex-mediated glomerulonephritis, lupus nephritis (LN), antineutrophil cytoplasmic antibodies (ANCA-) associated glomerulonephritis, minimal change disease, diabetic nephropathy (DN), acute kidney injury (AKI), obstructive uropathy, kidney allograft rejection, cisplatin-induced AKI and obstructive uropathy, eye diseases (including diabetic retinopathy, diabetic macular oedema, retinopathy of prematurity, age related macular degeneration, macular oedema, proliferative and/or non proliferative retinopathy, corneal vascularisation including neovascularization, retinal vein occlusion, various forms of uveitis and keratitis), thryoiditis, fibrosing disorders including various forms of hepatic fibrosis, various forms of pulmonary fibrosis, systemic sclerosis, scleroderma, cancer and cancer associated complications (including skeletal complications, cachexia and anaemia).

The antibodies and fragments according to the present disclosure may be employed in treatment or prophylaxis.

The present invention also provides a method of reducing the concentration of undesired antibodies in an individual comprising the steps of administering to an individual a therapeutically effective dose of an anti-TNF antibody or binding fragment thereof described herein.

The present invention further provides the use of an antibody molecule according to the present invention in the manufacture of a medicament for the treatment and/or prophylaxis of a pathological disorder described herein such as an autoimmune disease.

In one embodiment the present disclosure comprises use of antibodies or fragments thereof as a reagent for diagnosis, for example conjugated to a reporter molecule. Thus there is provided antibody or fragment according to the disclosure which is labelled. In one aspect there is provided a column comprising an antibody or fragment according to the disclosure.

Comprising in the context of the present specification is intended to meaning including.

Where technically appropriate embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

The present invention is further described by way of illustration only in the following examples, which refer to the accompanying Figures, in which:

EXAMPLES

Example 1

Isolation of Neutralizing Anti-Human TNF-Alpha Variable Regions

The following immunizations were performed in order to generate material for B cell culture and antibody screening:

5 Sprague Dawley rats were immunised with 3 shots of human TNF-alpha pre-complexed with a small molecule benzimidazole compound, Compound 1 (as described in WO2013/186229 and PCT/EP2015/074527). Sera was generated and tested for binding to human TNF-alpha in an ELISA. Titres were measurable beyond a 100,000 dilution and were therefore considered acceptable for B cell culturing.

B cell cultures were prepared using a method similar to that described by Zubler et al. (1985) and Lightwood et al. (2013). Briefly, splenocytes containing B cells, at a density of approximately 5000 cells per well were cultured in bar-coded 96-well tissue culture plates with 200 µl/well RPMI 1640 medium (Gibco BRL) supplemented with 10% FCS (PAA laboratories ltd), 2% HEPES (Sigma Aldrich), 1% L-Glutamine (Gibco BRL), 1% penicillin/streptomycin solution (Gibco BRL), 0.1% β-mercaptoethanol (Gibco BRL), 2-5% activated splenocyte culture supernatant and gamma-irradiated murine thymoma cells ($5 \times 10^4$/well) for seven days at 37° C. in an atmosphere of 5% $CO_2$. Over 70 million B cells were screened during this project.

The presence of human TNF-specific antibodies in B cell culture supernatants was determined using a homogeneous fluorescence-based binding assay using 10 micron superavidin polymeric beads (Bangs laboratories) coated with biotinylated human TNF as a source of target antigen. 10 ul of supernatant was transferred from barcoded 96-well tissue culture plates into barcoded 384-well black-walled assay plates containing 5000 the coated beads using a Matrix Platemate liquid handler. Binding was revealed with a goat anti-rat or mouse IgG Fcγ-specific Cy-5 conjugate (Jackson). Plates were read on an Applied Biosystems 8200 cellular detection system.

Alternatively, ELISA assays were used to identify positive wells. 384-well ELISA plates were coated with 2 ug/ml TNF before 10 ul of B cell culture supernatant was added to the blocked plate. Following incubation for 1 hour plates were washed and binding revealed with a goat anti-rat Fc-specific HRP conjugate (Jackson).

Following primary screening, positive supernatants were consolidated onto 96-well bar-coded master plates using an Aviso Onyx hit-picking robot and B cells in cell culture plates frozen at −80 C. Master plates were then screened in a Biacore assay in order to identify wells containing antibodies of high affinity.

In order to identify antibodies capable of neutralising the biological activity of TNFα, we performed a cell-based TNFα reporter assay using the B cell culture supernatants in master plates. The assay utilised HEK-293-CD40-BLUE cells (Invivogen) which are engineered to secrete alkaline phosphatase in response to a number of stimuli operating through the NFκB pathway including human TNFα. Antibody-containing supernatants were used directly in this assay at a single dilution of 1:2.5. Wells containing high affinity blocking antibodies (sub 100 pM in Biacore and showing >90% inhibition in the reporter assay) were selected for further progression.

To allow recovery of antibody variable region genes from a selection of wells of interest, a deconvolution step had to be performed to enable identification of the antigen-specific B cells in a given well that contained a heterogeneous population of B cells. This was achieved using the Fluorescent foci method. Briefly, Immunoglobulin-secreting B cells from a positive well were mixed with streptavidin beads (New England Biolabs) coated with biotinylated human TNF and a 1:1200 final dilution of a goat anti-rat Fcγ fragment-specific FITC conjugate (Jackson). After static incubation at 37° C. for 1 hour, antigen-specific B cells could be identified due to the presence of a fluorescent halo surrounding that B cell. These individual B cells, identified using an Olympus microscope, were then picked with an Eppendorf micromanipulator and deposited into a PCR tube.

Antibody variable region genes for four different antibodies known as 2102, 2101, 2109 and 2111 were recovered from single cells by reverse transcription (RT)-PCR using heavy and light chain variable region-specific primers. Two rounds of PCR were performed on an Aviso Onyx liquid handling robot, with the nested 2° PCR incorporating restriction sites at the 3' and 5' ends allowing cloning of the rat variable region into a mouse γ1 IgG or Fab (VH) or mouse kappa (VL) mammalian expression vector. Heavy and light chain constructs were co-transfected into HEK-293 cells using Fectin 293 (Invitrogen) and recombinant antibody expressed in 48-well plates in a volume of 1 ml. After 5-7 days expression, supernatants were harvested and antibody subject to further screening.

Recombinant rat/mouse chimeric IgG and Fab molecules were screened in the HEK-293-CD40-BLUE reporter assay at a number of concentrations to enable the calculation of EC50 values and determine the maximum percentage inhibition. Fab fragments were tested in order to ensure the antibody was active when monovalent. IgG were also analysed in a Biacore experiment to determine binding affinities for human TNF. The assay format of the Biacore experiment was capture of the mouse IgG by immobilised anti-mouse IgG-Fc then titration of human TNF over the captured surface. BIA (Biamolecular Interaction Analysis) was performed using a Biacore T200 (GE Healthcare). Affinipure F(ab')2 Fragment goat anti-mouse IgG, Fc fragment specific (Jackson ImmunoResearch) was immobilised on a CM5 Sensor Chip via amine coupling chemistry to a level of ~5000 response units (RUs). HBS-EP buffer (10 mM HEPES pH 7.4, 0.15 M NaCl, 3 mM EDTA, 0.05% Surfactant P20, GE Healthcare) was used as the running buffer with a flow rate of 10 µL/min. A 10 µinjection of mouse IgG at 0.5 µg/mL was used for capture by the immobilised anti-mouse IgG-Fc. Human TNF, was injected over the captured mouse IgG twice at 20 nM at a flow rate of 30 µL/min. The surface was regenerated by 2×10 µL injection of 40 mM HCl, interspersed by a 5 µL injection of 5 mM NaOH at a flowrate of 10 µL/min. Background subtraction binding curves were analysed using the T200evaluation software (version 1.0) following standard procedures.

TABLE 1

| Antibody | EC50 (ng/ml) | % inhibition | ka (1/Ms) | kd (1/s) | KD (pM) |
|---|---|---|---|---|---|
| CA2109 IgG | 0.31 | 100 | 4.70E+06 | 1.19E−04 | 25 |
| CA2109 Fab | 3.8 | 100 | ND | ND | ND |

Neutralisation was determined using the HEK-293-CD40-BLUE reporter assay (Invivogen). EC50 and % neutralisation is shown. Biacore analysis was performed to determine binding kinetics. On rate (ka), off rate (kd) and affinity constant (KD) are shown.

Figure 2B:
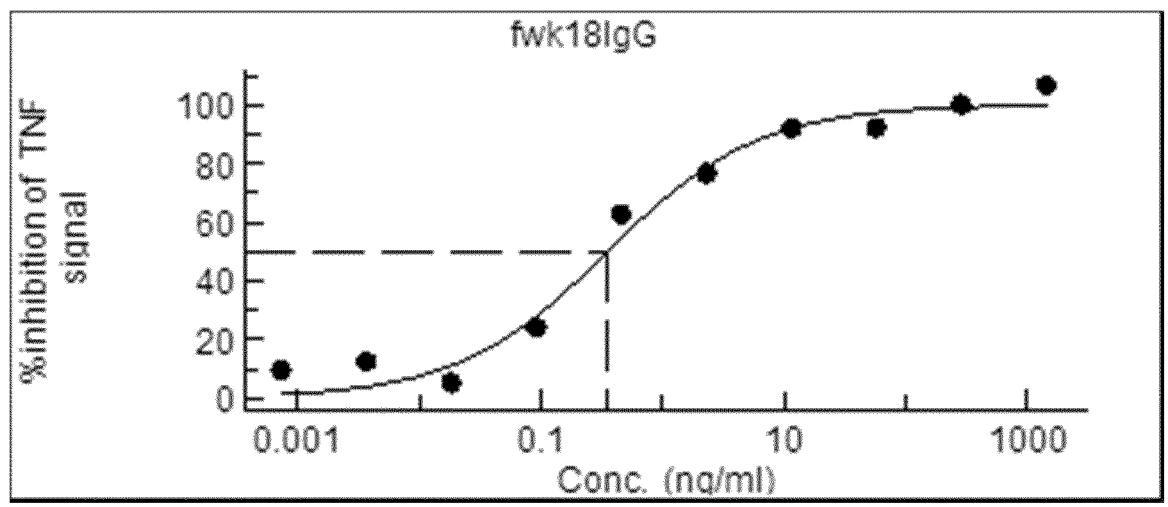

FIG. 2 shows the Titration curves for CA2109 rat/mouse Fab (fwk18 FAB) IgG1 (fwk18 IgG). Data determined using the HEK-293-CD40-BLUE reporter assay (Invivogen) as described above.

All four antibodies (2101, 2109, 2111 and 2102) isolated as described above were screened as rat/human chimeric Fabs for cyno and human TNF cross-reactivity on human TNF (hTNF) and cyno TNF (cTNF) as shown in Table 1a below.

The assay format of the Biacore experiment was capture of the rat/human chimeric Fabs by immobilised anti-human F(ab') then titration of human or cynomolgus TNF over the captured surface. BIA (Biamolecular Interaction Analysis) was performed using a Biacore T200 (GE Healthcare). Affinipure F(ab')2 Fragment goat anti-human IgG-F(ab')2 fragment specific (Jackson ImmunoResearch) was immobilised on a CM5 Sensor Chip via amine coupling chemistry to a level of ~5000 response units (RUs). HBS-EP buffer (10 mM HEPES pH 7.4, 0.15 M NaCl, 3 mM EDTA, 0.05% Surfactant P20, GE Healthcare) was used as the running buffer with a flow rate of 10 µL/min. A 10 µL injection of rat/human chimeric at 0.5 µg/mL was used for capture by the immobilised human IgG-F(ab')2. Human or cynomolgus TNF, was injected over the captured rat/human chimeric Fab at (5 nM or 3.125 nM respectively) at a flow rate of 30 µL/min. The surface was regenerated by 2×10 µL injection of 50 mM HCl, interspersed by a 5 µL injection of 5 mM NaOH at a flowrate of 10 µL/min. Background subtraction binding curves were analysed using the T200evaluation software (version 1.0) following standard procedures.

TABLE 1a

|  |  |  | ka (1/Ms) | kd (1/s) | KD (M) | KD (pM) |
|---|---|---|---|---|---|---|
| 02101 | human Fab chimeric | hTNF | 4.63E+06 | 1.39E−04 | 2.99E−11 | 30 |
| 02109 | human Fab chimeric | hTNF | 4.09E+06 | 1.43E−04 | 3.49E−11 | 35 |
| 02111 | human Fab chimeric | hTNF | 2.89E+06 | 1.39E−04 | 4.81E−11 | 48 |
| 02102 | human Fab chimeric | hTNF | 2.59E+06 | 2.27E−04 | 8.73E−11 | 87 |
| 02101 | human Fab chimeric | cTNF | 4.54E+06 | 9.72E−05 | 2.14E−11 | 21 |
| 02109 | human Fab chimeric | cTNF | 3.71E+06 | 1.02E−04 | 2.74E−11 | 27 |
| 02111 | human Fab chimeric | cTNF | 2.26E+06 | 2.25E−04 | 9.98E−11 | 100 |
| 02102 | human Fab chimeric | cTNF | 4.17E+05 | 8.64E−03 | 2.07E−08 | 20720 |

Antibody 2102 was found to have a much lower affinity for cyno TNF. This antibody also lost affinity during humanisation so was not progressed any further.

Based on this work, CA2109 was selected as a lead candidate due to its cyno/human cross reactivity (Table 1a), high affinity (Table 1) and potent neutralisation activity (FIG. 2 and Table 1). This antibody was selected for humanisation based on these properties.

Two other antibodies having similar affinity and neutralisation properties were selected for humanisation in parallel to CA2109, these were 2101 and 2111. However, 2101 failed to retain affinity for TNF upon humanisation so this antibody was not progressed any further. Antibody 2109 and antibody 2111 were both successfully humanised and then converted to a scFv format and screened in an L929 TNF inhibition assay (assay described below) to confirm neutralisation activity (Table 2).

TABLE 2

| Antibody | IC50 (pM) |
|---|---|
| CA2111 Fab | 12.49 |
| CA2111 VH1 HLds scFv | 135.09 |
| CA2111 VH1 LHds scFv | 143.24 |
| CA2109 VH3 scFv | 16.55 |

The L929 cell line is a murine fibrosarcoma cell line which is sensitive to the cytotoxic effects of TNF-α. TNF stimulates via the TNF receptors, which bind Human, Cynomolgus or Murine TNF-α, to induce apoptosis. Cells are co-treated with Actinomycin D which increases the susceptibility to killing by TNF-α. The viability of the L929 cells following treatment with Actinomycin-D/TNF-α and each anti-TNF antibody was determined by detecting ATP levels (which decrease with decreasing viability) via a luciferase reaction (CellTiter-Glo, Promega).

L929 cells were treated with 2.35 µg/ml Actinomycin D and human TNF alpha at 100 pg/ml in the presence of each antibody or control compound in a final volume of 30 µl in a 384 well flat bottom plate, following a 1 hour pre-incubation. After 24 hours at 37° C., 5% CO2 cell viability was measured by CellTiter-Glo (Promega Ltd).

As can be seen in Table 2, Antibody 2111 did not retain activity in this assay as a scFv (compared to the humanised Fab) in either the heavy-light (HL) or light-heavy (LH) orientation. Only antibody 2109 retained cyno-human cross reactivity, high affinity and neutralisation capability and thermostability as a humanised scFv. The humanisation of antibody CA2109 is described in more detail below.

Example 2

Humanization of Anti-TNF-Alpha Antibody CA2109

Antibody CA2109 was humanised by grafting the complementarity determining regions (CDR) onto human germline frameworks. Alignments of the rat antibody (donor) sequence with the human germline (acceptor) frameworks are shown in FIGS. 3 and 4, together with the designed humanised sequences.

The light chain germline acceptor sequence chosen was the human VK1 2-1(U) A20 V-region plus JK2 J-region (V BASE, vbase.mrc-cpe.cam.ac.uk/). The heavy chain germline acceptor sequence chosen was the human VH3 1-3 3-21 V-region plus JH4 J-region (V BASE, vbase.mrc-cpe.cam.ac.uk/). The CDRs grafted from the donor to the acceptor sequence are as defined by Kabat (Kabat et al. 1987), with the exception of CDR-H1 where the combined Chothia/Kabat definition is used.

Genes encoding initial V-region sequences were designed and constructed by an automated synthesis approach by Entelechon GmbH, and modified to generate the grafted versions gL1, gL 18, gH1 and gH2 by oligonucleotide directed mutagenesis. The gL18 gene sequence was sub-cloned into the UCB Celltech human light chain expression vector pMhCK delta, which contains DNA encoding the human C-Kappa constant region (Km3 allotype). The gH2 sequence was sub-cloned into the UCB Celltech expression vector pMhg1Fab, which contains DNA encoding human heavy chain gamma-1 CH1 constant region.

In order to retain full activity and maintain high thermostability, donor residues at positions 48 (Isoleucine), 49 (Glycine), 71 (Valine), 73 (Lysine), 78 (Alanine) and 93 (Threonine) of the humanised heavy chain (Kabat numbering) were retained. Similarly, donor residues at positions 65 (Threonine), 71 (Tyrosine) and 87 (Phenylalanine) of the humanised light chain (Kabat numbering) were retained. In addition, 3 deamidation sites in the light chain were removed by mutating Asparagine residues at positions 31, 50 and 52 to Serine, Aspartic acid and Serine, respectively. The final selected variable graft sequences gL18 and gH2 are shown in FIGS. 1, 3 and 4, SEQ ID NO: 11 and 12.

As described above in Example 1, only antibody 2109 retained cyno-human cross reactivity, high affinity and neutralisation capability and thermostability as a humanised scFv. The ability of antibody 2109 to be equally active in multiple antibody formats including IgG, Fab and scFv makes this a useful and versatile antibody which may be used alone as a mono-specific antibody or be incorporated into multi-specific antibody formats.

The invention claimed is:

1. An anti-TNF antibody or binding fragment thereof comprising a heavy chain or heavy chain fragment having a variable region comprising three CDRs, wherein CDR H1 has the sequence given in SEQ ID NO: 1, CDR H2 has the sequence given in SEQ ID NO: 2, and CDR H3 has the sequence given in SEQ ID NO: 3, and comprising a light chain or fragment thereof having a variable region comprising three CDRs, wherein CDR L1 has the sequence given in SEQ ID NO: 4 or 5, CDR L2 has the sequence given in SEQ ID NO: 6, 7, 8 or 9, and CDR L3 has the sequence given in SEQ ID NO: 10.

2. The anti-TNF antibody or binding fragment thereof according to claim 1 wherein the heavy chain or heavy chain fragment comprises a variable region comprising the sequence given in SEQ ID NO: 12 or 16 and the light chain or light chain fragment comprises a variable region comprising the sequence given in SEQ ID NO: 11 or 15.

3. The anti-TNF antibody or binding fragment thereof according to claim 2, having a heavy chain comprising the sequence given in SEQ ID NO:
12 and a light chain comprising the sequence given in SEQ ID NO: 11.

4. The anti-TNF antibody or binding fragment thereof according to claim 2, having a heavy chain comprising the sequence given in SEQ ID NO: 16 and a light chain comprising the sequence given in SEQ ID NO: 15.

5. The anti-TNF antibody or binding fragment thereof according to claim 2, wherein the antibody or binding fragment is a scFv, dsscFv Fv, Fab, Fab', Fab-Fv, or Fab-dsFv fragment.

6. The anti-TNF antibody or binding fragment thereof according to claim 2, wherein the antibody or binding fragment is conjugated to a polymer selected from starch, albumin and polyethylene glycol (PEG).

7. The anti-TNF antibody or binding fragment thereof according to claim 6, wherein the polymer is PEG with a molecular weight in the range 5 to 50 kDa.

8. The anti-TNF antibody according to claim 2, wherein the antibody is a full length antibody.

9. The anti-TNF antibody according to claim 8, wherein the full length antibody is selected from the group consisting of an IgG1, IgG4 and IgG4P.

10. The anti-TNF antibody or binding fragment thereof of claim 3 which is full length antibody selected from the group consisting of an IgG1, IgG4 and IgG4P.

11. The anti-TNF antibody or binding fragment thereof of claim 4 which is full length antibody selected from the group consisting of an IgG1, IgG4 and IgG4P.

12. The anti-TNF antibody or binding fragment thereof according to claim 2, which has a binding affinity for human TNF of 150 pM or higher affinity.

13. An isolated DNA sequence encoding the heavy and/or light chain(s) of an antibody according to claim 2.

14. A cloning or expression vector comprising one or more DNA sequences according to claim 13.

15. The vector according to claim 14, wherein the vector comprises (i) the sequence given in SEQ ID NO: 17, 18 and/or 22.

16. A host cell comprising one or more cloning or expression vectors according to claim 14.

17. A process for the production of an antibody having binding specificity for human TNF, comprising culturing the host cell of claim 16 and isolating the antibody.

18. A pharmaceutical composition comprising an anti-TNF antibody or binding fragment thereof as defined in claim 2 in combination with one or more of a pharmaceutically acceptable excipient, diluent or carrier.

19. A pharmaceutical composition according to claim 18 comprising other active ingredients.

20. A method of treating a patient suffering from an autoimmune or inflammatory disorder mediated by TNFα, the method comprising administering to the patient a therapeutically effective amount of an antibody or binding fragment thereof as defined in claim 2.

21. The method of claim 20, wherein the antibody or binding fragment thereof comprises having a heavy chain comprising the sequence given in SEQ ID NO: 12 and a light chain comprising the sequence given in SEQ ID NO: 11.

22. The method of claim 20, wherein the antibody or binding fragment thereof comprises having a heavy chain comprising the sequence given in SEQ ID NO: 16 and a light chain comprising the sequence given in SEQ ID NO: 15.

* * * * *

SEQUENCE LISTING

```
<160> NUMBER OF SEQ ID NOS: 37

<210> SEQ ID NO 1
<211> LENGTH: 10
<212> TYPE: PRT
<213> ORGANISM: Artificial Sequence
<220> FEATURE:
<223> OTHER INFORMATION: CDR sequences of antibody 2109 - CDRH1

<400> SEQUENCE: 1

Gly Tyr Thr Phe Thr Asp Asn Tyr Ile His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDR sequences of antibody 2109 - CDRH2

<400> SEQUENCE: 2

Tyr Ile Asn Pro Ser Ser Ala Tyr Ala His Tyr Asn Glu Lys Phe Lys
1               5                   10                  15

Thr

<210> SEQ ID NO 3
<211> LENGTH: 10
<212> TYPE: PRT
<213> ORGANISM: Artificial Sequence
<220> FEATURE:
```

```
<223> OTHER INFORMATION: CDR sequences of antibody 2109 - CDRH3

<400> SEQUENCE: 3

Arg Tyr Tyr Ser Ala Met Pro Phe Ala Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CDR sequences of antibody 2109 - CDRL1

<400> SEQUENCE: 4

Arg Ala Ser Glu Asp Ile Tyr Ser Gly Leu Ala
1               5                   10

<210> SEQ ID NO 5
<211> LENGTH: 11
<212> TYPE: PRT
<213> ORGANISM: Artificial Sequence
<220> FEATURE:
<223> OTHER INFORMATION: CDR sequences of antibody 2109 - CDRL1

<400> SEQUENCE: 5

Arg Ala Ser Glu Asp Ile Tyr Asn Gly Leu Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: CDR sequences of antibody 2109 - CDRL2

<400> SEQUENCE: 6

Asp Ser Ser Thr Leu His Thr
1               5

<210> SEQ ID NO 7
<211> LENGTH: 7
<212> TYPE: PRT
<213> ORGANISM: Artificial Sequence
<220> FEATURE:
<223> OTHER INFORMATION: CDR sequences of antibody 2109 - CDRL2

<400> SEQUENCE: 7

Asn Ser Asn Thr Leu His Thr
1               5

<210> SEQ ID NO 8
<211> LENGTH: 7
<212> TYPE: PRT
<213> ORGANISM: Artificial Sequence
<220> FEATURE:
<223> OTHER INFORMATION: CDR sequences of antibody 2109 - CDRL2

<400> SEQUENCE: 8

Asn Ser Ser Thr Leu His Thr
1               5

<210> SEQ ID NO 9
<211> LENGTH: 7
<212> TYPE: PRT
<213> ORGANISM: Artificial Sequence
<220> FEATURE:
<223> OTHER INFORMATION: CDR sequences of antibody 2109  - CDRL2
```

```
<400> SEQUENCE: 9

Asp Ser Asn Thr Leu His Thr
1               5

<210> SEQ ID NO 10
<211> LENGTH: 9
<212> TYPE: PRT
<213> ORGANISM: Artificial Sequence
<220> FEATURE:
<223> OTHER INFORMATION: CDR sequences of antibody 2109 - CDRL3

<400> SEQUENCE: 10

Gln Gln Asn Tyr Asp Phe Pro Leu Thr
1               5

<210> SEQ ID NO 11
<211> LENGTH: 109
<212> TYPE: PRT
<213> ORGANISM: Artificial Sequence
<220> FEATURE:
<223> OTHER INFORMATION: Light Chain variable region of antibody 2109
      gL18

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Ser Gly
            20                  25                  30

Leu Ala Trp Tyr Gln Gln Lys Pro Gly Lys Val Pro Lys Leu Leu Ile
        35                  40                  45

Tyr Asp Ser Ser Thr Leu His Thr Gly Val Pro Ser Arg Phe Ser Gly
    50                  55                  60

Thr Gly Ser Gly Thr Asp Tyr Thr Leu Thr Ile Ser Ser Leu Gln Pro
65                  70                  75                  80

Glu Asp Val Ala Thr Tyr Phe Cys Gln Gln Asn Tyr Asp Phe Pro Leu
                85                  90                  95

Thr Phe Gly Gln Gly Thr Lys Leu Glu Ile Lys Arg Thr
            100                 105

<210> SEQ ID NO 12
<211> LENGTH: 119
<212> TYPE: PRT
<213> ORGANISM: Artificial Sequence
<220> FEATURE:
<223> OTHER INFORMATION: Heavy Chain variable region of antibody 2109
      gH2

<400> SEQUENCE: 12

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Asp Asn
            20                  25                  30

Tyr Ile His Trp Val Arg Gln Ala Pro Gly Lys Gly Leu Glu Trp Ile
        35                  40                  45

Gly Tyr Ile Asn Pro Ser Ser Ala Tyr Ala His Tyr Asn Glu Lys Phe
    50                  55                  60

Lys Thr Arg Phe Thr Ile Ser Val Asp Lys Ala Lys Asn Ser Ala Tyr
65                  70                  75                  80

Leu Gln Met Asn Ser Leu Arg Ala Glu Asp Thr Ala Val Tyr Tyr Cys
                85                  90                  95
```

```
Thr Arg Arg Tyr Tyr Ser Ala Met Pro Phe Ala Tyr Trp Gly Gln Gly
            100                 105                 110

Thr Leu Val Thr Val Ser Ser
        115

<210> SEQ ID NO 13
<211> LENGTH: 327
<212> TYPE: DNA
<213> ORGANISM: Artificial Sequence
<220> FEATURE:
<223> OTHER INFORMATION: DNA encoding Light Chain variable region of
      antibody 2109 gL18

<400> SEQUENCE: 13
gatatacaga tgacccaatc accaagctct ctgagtgctt ccgttggcga tcgcgttaca      60
attacctgcc gagctagcga ggatatatac tcaggactgg cctggtacca gcaaaagcct    120
ggcaaagtgc ctaagctcct gatctacgac tccagtaccc tgcacactgg tgtgccaagc    180
cgctttagcg gaactggatc tggaaccgac tatacactga cgattcctc actgcaaccg     240 gaagacgtgg caacctactt ctgtcagcaa aactacgact tccccttgac gtttgggcaa    300
gggacaaagc tggagatcaa acgtacc                                         327

<210> SEQ ID NO 14
<211> LENGTH: 357
<212> TYPE: DNA
<213> ORGANISM: Artificial Sequence
<220> FEATURE:
<223> OTHER INFORMATION: DNA encoding Heavy Chain variable region of
      antibody 2109 gH2

<400> SEQUENCE: 14
gaagttcaac tggtcgaaag cggaggtggg ctcgtgaaac ctggcggatc tctgcgattg     60
tcatgtgctg caagcggcta cacgtttacc gataactata tccactgggt gcgacaagca    120
ccagggaagg gactggaatg gattggatat attaacccga gctccgccta cgcacactac    180
aacgagaaat tcaagacccg attcaccatc tccgtggaca agccaagaa ctccgcttac     240 ctgcaaatga actctctgcg ggccgaagac actgccgtgt attactgcac cgccgatac     300 tatagcgcta tgcccttttgc ctactgggga caagggacac tggtcactgt ctcaagt      357

<210> SEQ ID NO 15
<211> LENGTH: 109
<212> TYPE: PRT
<213> ORGANISM: Artificial Sequence
<220> FEATURE:
<223> OTHER INFORMATION: Light Chain variable region of antibody 2109
      gL18

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Ser Gly
            20                  25                  30

Leu Ala Trp Tyr Gln Gln Lys Pro Gly Lys Val Pro Lys Leu Leu Ile
        35                  40                  45

Tyr Asp Ser Ser Thr Leu His Thr Gly Val Pro Ser Arg Phe Ser Gly
    50                  55                  60

Thr Gly Ser Gly Thr Asp Tyr Thr Leu Thr Ile Ser Ser Leu Gln Pro
65                  70                  75                  80
```

Glu Asp Val Ala Thr Tyr Phe Cys Gln Gln Asn Tyr Asp Phe Pro Leu
                85                  90                  95

Thr Phe Gly Cys Gly Thr Lys Leu Glu Ile Lys Arg Thr
        100                 105

<210> SEQ ID NO 16
<211> LENGTH: 119
<212> TYPE: PRT
<213> ORGANISM: Artificial Sequence
<220> FEATURE:
<223> OTHER INFORMATION: Heavy Chain variable region of antibody 2109
      gH2

<400> SEQUENCE: 16

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Asp Asn
            20                  25                  30

Tyr Ile His Trp Val Arg Gln Ala Pro Gly Lys Cys Leu Glu Trp Ile
        35                  40                  45

Gly Tyr Ile Asn Pro Ser Ser Ala Tyr Ala His Tyr Asn Glu Lys Phe
    50                  55                  60

Lys Thr Arg Phe Thr Ile Ser Val Asp Lys Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Thr Arg Arg Tyr Tyr Ser Ala Met Pro Phe Ala Tyr Trp Gly Gln Gly
            100                 105                 110

Thr Leu Val Thr Val Ser Ser
        115

<210> SEQ ID NO 17
<211> LENGTH: 327
<212> TYPE: DNA
<213> ORGANISM: Artificial Sequence
<220> FEATURE:
<223> OTHER INFORMATION: DNA encoding Light Chain variable region of
      antibody 2109 gL18

<400> SEQUENCE: 17
gatatccaga tgacccagtc gccgtccagc ctctccgcct ccgtgggaga cagagtgacg      60
atcacttgca gagcatcaga ggacatctac tctggccttg cttggtatca gcagaagccg     120
ggaaaggtgc ccaaactgct catctatgac tcctcgaccc tccacacggg agtgccatcg     180
cgcttcagcg ggaccggatc tgggaccgac tacaccctga ccatttcatc gctccagccg     240
gaggatgttg ccacttactt ctgccaacag aattacgact cccacttac ttttggatgt      300 ggcactaagc tcgaaatcaa gcgcacc                                         327

<210> SEQ ID NO 18
<211> LENGTH: 357
<212> TYPE: DNA
<213> ORGANISM: Artificial Sequence
<220> FEATURE:
<223> OTHER INFORMATION: DNA encoding Heavy Chain variable region of
      antibody 2109 gH2

<400> SEQUENCE: 18
gaagtgcagt tggtggagtc ggggggaggg ttggtgaagc caggaggatc attgcggttg      60
tcatgtgcgg cttcgggcta cactttcact gacaattaca ttcactgggt gcgacaagca     120

| ccagggaagt | gcctcgaatg | gattggctac | atcaacccgt | caagcgcata | cgcccattac | 180 |
| aacgaaaagt | tcaagacccg | gttcaccatc | tccgtggata | aggcgaaaaa | cagcgcgtac | 240 |
| cttcagatga | actccctgcg | ggccgaggat | accgccgttt | actactgcac | tagacggtac | 300 |
| tacagcgcca | tgccgttcgc | gtactgggga | caaggcactc | tggtcaccgt | gtcgtcg | 357 |

<210> SEQ ID NO 19
<211> LENGTH: 248
<212> TYPE: PRT
<213> ORGANISM: Artificial Sequence
<220> FEATURE:
<223> OTHER INFORMATION: scFv (VH-VL) of antibody 2109 gH2gL18

<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Asp Asn
            20                  25                  30

Tyr Ile His Trp Val Arg Gln Ala Pro Gly Lys Gly Leu Glu Trp Ile
        35                  40                  45

Gly Tyr Ile Asn Pro Ser Ser Ala Tyr Ala His Tyr Asn Glu Lys Phe
    50                  55                  60

Lys Thr Arg Phe Thr Ile Ser Val Asp Lys Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Thr Arg Arg Tyr Tyr Ser Ala Met Pro Phe Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Glu Asp Ile Tyr Ser Gly Leu Ala Trp Tyr Gln
                165                 170                 175

Gln Lys Pro Gly Lys Val Pro Lys Leu Leu Ile Tyr Asp Ser Ser Thr
            180                 185                 190

Leu His Thr Gly Val Pro Ser Arg Phe Ser Gly Thr Gly Ser Gly Thr
        195                 200                 205

Asp Tyr Thr Leu Thr Ile Ser Ser Leu Gln Pro Glu Asp Val Ala Thr
    210                 215                 220

Tyr Phe Cys Gln Gln Asn Tyr Asp Phe Pro Leu Thr Phe Gly Gln Gly
225                 230                 235                 240

Thr Lys Leu Glu Ile Lys Arg Thr
                245

<210> SEQ ID NO 20
<211> LENGTH: 744
<212> TYPE: DNA
<213> ORGANISM: Artificial Sequence
<220> FEATURE:
<223> OTHER INFORMATION: DNA encoding scFv (VH-VL) of antibody 2109
      gH2gL18

<400> SEQUENCE: 20

| gaagttcaac | tggtcgaaag | cggaggtggg | ctcgtgaaac | ctggcggatc | tctgcgattg | 60 |

```
tcatgtgctg caagcggcta cacgtttacc gataactata tccactgggt gcgacaagca    120
ccagggaagg gactggaatg gattggatat attaacccga gctccgccta cgcacactac    180
aacgagaaat tcaagacccg attcaccatc tccgtggaca agccaagaa ctccgcttac     240 ctgcaaatga actctctgcg ggccgaagac actgccgtgt attactgcac cgccgatac    300 tatagcgcta tgccctttgc ctactgggga caagggacac tggtcactgt ctcaagtgga    360
ggtggcggtt ctggcggtgg cggttccggt ggcggtggat cgggaggtgg cggttctgat    420
atacagatga cccaatcacc aagctctctg agtgcttccg ttggcgatcg cgttacaatt    480
acctgccgag ctagcgagga tatatactca ggactggcct ggtaccagca aaagcctggc    540
aaagtgccta agctcctgat ctacgactcc agtaccctgc acactggtgt gccaagccgc    600
tttagcggaa ctggatctgg aaccgactat acactgacga tttcctcact gcaaccggaa    660
gacgtggcaa cctacttctg tcagcaaaac tacgacttcc ccttgacgtt tgggcaaggg    720
acaaagctgg agatcaaacg tacc                                           744
```

<210> SEQ ID NO 21
<211> LENGTH: 248
<212> TYPE: PRT
<213> ORGANISM: Artificial Sequence
<220> FEATURE:
<223> OTHER INFORMATION: dsscFv (VH-VL) of antibody 2109 gH2gL18

<400> SEQUENCE: 21

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Asp Asn
            20                  25                  30

Tyr Ile His Trp Val Arg Gln Ala Pro Gly Lys Cys Leu Glu Trp Ile
        35                  40                  45

Gly Tyr Ile Asn Pro Ser Ser Ala Tyr Ala His Tyr Asn Glu Lys Phe
    50                  55                  60

Lys Thr Arg Phe Thr Ile Ser Val Asp Lys Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Thr Arg Arg Tyr Tyr Ser Ala Met Pro Phe Ala Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Glu Asp Ile Tyr Ser Gly Leu Ala Trp Tyr Gln
                165                 170                 175

Gln Lys Pro Gly Lys Val Pro Lys Leu Leu Ile Tyr Asp Ser Ser Thr
            180                 185                 190

Leu His Thr Gly Val Pro Ser Arg Phe Ser Gly Thr Gly Ser Gly Thr
        195                 200                 205

Asp Tyr Thr Leu Thr Ile Ser Ser Leu Gln Pro Glu Asp Val Ala Thr
    210                 215                 220

Tyr Phe Cys Gln Gln Asn Tyr Asp Phe Pro Leu Thr Phe Gly Cys Gly
225                 230                 235                 240
```

-continued

```
Thr Lys Leu Glu Ile Lys Arg Thr
            245
```

<210> SEQ ID NO 22
<211> LENGTH: 744
<212> TYPE: DNA
<213> ORGANISM: Artificial Sequence
<220> FEATURE:
<223> OTHER INFORMATION: DNA encoding dsscFv (VH-VL) of antibody 2109
      gH2gL18

<400> SEQUENCE: 22

```
gaagtgcagt tggtggagtc ggggggaggg ttggtgaagc caggaggatc attgcggttg    60
tcatgtgcgg cttcgggcta cactttcact gacaattaca ttcactgggt gcgacaagca   120
ccagggaagt gcctcgaatg gattggctac atcaacccgt caagcgcata cgcccattac   180
aacgaaaagt tcaagacccg gttcaccatc tccgtggata aggcgaaaaa cagcgcgtac   240
cttcagatga actccctgcg ggccgaggat accgccgttt actactgcac tagacggtac   300
tacagcgcca tgccgttcgc gtactgggga caaggcactc tggtcaccgt gtcgtcggga   360
ggaggaggct cgggtggagg cggatcgggt ggcggaggga gcggcggagg cggttcggat   420
atccagatga cccagtcgcc gtccagcctc tccgcctccg tgggagacag agtgacgatc   480
acttgcagag catcagagga catctactct ggccttgctt ggtatcagca gaagccggga   540
aaggtgccca aactgctcat ctatgactcc tcgaccctcc acacgggagt gccatcgcgc   600
ttcagcggga ccggatctgg gaccgactac accctgacca tttcatcgct ccagccggag   660
gatgttgcca cttacttctg ccaacagaat tacgacttcc cacttacttt tggatgtggc   720
actaagctcg aaatcaagcg cacc                                          744
```

<210> SEQ ID NO 23
<211> LENGTH: 107
<212> TYPE: PRT
<213> ORGANISM: Artificial Sequence
<220> FEATURE:
<223> OTHER INFORMATION: Light Chain variable region of rat antibody
      2109

<400> SEQUENCE: 23

```
Asp Ile Val Met Thr Gln Ser Pro Ala Ser Leu Ser Ala Ser Leu Gly
1               5                   10                  15
Glu Thr Val Thr Ile Glu Cys Arg Ala Ser Glu Asp Ile Tyr Asn Gly
            20                  25                  30
Leu Ala Trp Tyr Gln Gln Lys Pro Gly Lys Ser Pro His Leu Leu Ile
        35                  40                  45
Tyr Asn Ser Asn Thr Leu His Thr Gly Val Pro Ser Arg Phe Ser Gly
    50                  55                  60
Thr Gly Ser Gly Thr Gln Tyr Ser Leu Lys Ile Asn Ser Leu Gln Ser
65                  70                  75                  80
Glu Asp Val Ala Thr Tyr Phe Cys Gln Gln Asn Tyr Asp Phe Pro Leu
                85                  90                  95
Thr Phe Gly Ser Gly Thr Lys Leu Glu Leu Lys
            100                 105
```

<210> SEQ ID NO 24
<211> LENGTH: 119
<212> TYPE: PRT
<213> ORGANISM: Artificial Sequence
<220> FEATURE:
<223> OTHER INFORMATION: Heavy Chain variable region of rat antibody

2109

<400> SEQUENCE: 24

Glu Val Gln Leu His Gln Ser Gly Ala Ala Leu Val Lys Pro Gly Ala
1               5                   10                  15

Ser Val Lys Leu Ser Cys Lys Thr Ser Gly Tyr Thr Phe Thr Asp Asn
            20                  25                  30

Tyr Ile His Trp Val Lys Gln Ser Pro Gly Lys Ser Leu Glu Trp Ile
        35                  40                  45

Gly Tyr Ile Asn Pro Ser Ser Ala Tyr Ala His Tyr Asn Glu Lys Phe
    50                  55                  60

Lys Thr Lys Ala Thr Leu Thr Val Asp Lys Ser Thr Asn Thr Ala Tyr
65                  70                  75                  80

Met Glu Leu Ser Arg Leu Thr Ser Glu Asp Ser Ala Thr Tyr Phe Cys
                85                  90                  95

Thr Arg Arg Tyr Tyr Ser Ala Met Pro Phe Ala Tyr Trp Gly Gln Gly
            100                 105                 110

Thr Leu Val Thr Val Ser Ser
        115

<210> SEQ ID NO 25
<211> LENGTH: 107
<212> TYPE: PRT
<213> ORGANISM: Artificial Sequence
<220> FEATURE:
<223> OTHER INFORMATION: Human VK1 2-1(U) A20 JK2 acceptor framework

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Lys Leu Glu Ile Lys
            100                 105

<210> SEQ ID NO 26
<211> LENGTH: 113
<212> TYPE: PRT
<213> ORGANISM: Artificial Sequence
<220> FEATURE:
<223> OTHER INFORMATION: Human VH3 1-3 3-21 JH4 acceptor framework

<400> SEQUENCE: 26

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Thr Ser Tyr Ile Tyr Tyr Ala Asp Ser Val

```
                50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Phe Asp Tyr Trp Gly Gln Gly Thr Leu Val Thr Val Ser
                100                 105                 110

Ser

<210> SEQ ID NO 27
<211> LENGTH: 107
<212> TYPE: PRT
<213> ORGANISM: Artificial Sequence
<220> FEATURE:
<223> OTHER INFORMATION: Light Chain variable region of antibody 2109
      gL1

<400> SEQUENCE: 27

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asp Ile Tyr Asn Gly
                20                  25                  30

Leu Ala Trp Tyr Gln Gln Lys Pro Gly Lys Val Pro Lys Leu Leu Ile
             35                  40                  45

Tyr Asn Ser Asn Thr Leu His Thr Gly Val Pro Ser Arg Phe Ser Gly
         50                  55                  60

Thr Gly Ser Gly Thr Asp Tyr Thr Leu Thr Ile Ser Ser Leu Gln Pro
 65                  70                  75                  80

Glu Asp Val Ala Thr Tyr Phe Cys Gln Gln Asn Tyr Asp Phe Pro Leu
                 85                  90                  95

Thr Phe Gly Gln Gly Thr Lys Leu Glu Ile Lys
                100                 105

<210> SEQ ID NO 28
<211> LENGTH: 119
<212> TYPE: PRT
<213> ORGANISM: Artificial Sequence
<220> FEATURE:
<223> OTHER INFORMATION: Heavy Chain variable region of antibody 2109
      gH1

<400> SEQUENCE: 28

Glu Val Gln Leu Val Glu Ser Gly Gly Gly Leu Val Lys Pro Gly Gly
 1               5                  10                  15

Ser Leu Arg Leu Ser Cys Ala Thr Ser Gly Tyr Thr Phe Thr Asp Asn
                20                  25                  30

Tyr Ile His Trp Val Arg Gln Ala Pro Gly Lys Gly Leu Glu Trp Ile
             35                  40                  45

Gly Tyr Ile Asn Pro Ser Ser Ala Tyr Ala His Tyr Asn Glu Lys Phe
         50                  55                  60

Lys Thr Arg Phe Thr Ile Ser Val Asp Lys Ala Lys Asn Ser Ala Tyr
 65                  70                  75                  80

Leu Gln Met Asn Ser Leu Arg Ala Glu Asp Thr Ala Val Tyr Tyr Cys
                 85                  90                  95

Thr Arg Arg Tyr Tyr Ser Ala Met Pro Phe Ala Tyr Trp Gly Gln Gly
                100                 105                 110

Thr Leu Val Thr Val Ser Ser
            115
```

```
<210> SEQ ID NO 29
<211> LENGTH: 107
<212> TYPE: PRT
<213> ORGANISM: Artificial Sequence
<220> FEATURE:
<223> OTHER INFORMATION: Light Chain variable region of antibody 2109
      gL18

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Ser Gly
            20                  25                  30

Leu Ala Trp Tyr Gln Gln Lys Pro Gly Lys Val Pro Lys Leu Leu Ile
        35                  40                  45

Tyr Asp Ser Ser Thr Leu His Thr Gly Val Pro Ser Arg Phe Ser Gly
    50                  55                  60

Thr Gly Ser Gly Thr Asp Tyr Thr Leu Thr Ile Ser Ser Leu Gln Pro
65                  70                  75                  80

Glu Asp Val Ala Thr Tyr Phe Cys Gln Gln Asn Tyr Asp Phe Pro Leu
                85                  90                  95

Thr Phe Gly Gln Gly Thr Lys Leu Glu Ile Lys
            100                 105

<210> SEQ ID NO 30
<211> LENGTH: 324
<212> TYPE: PRT
<213> ORGANISM: Artificial Sequence
<220> FEATURE:
<223> OTHER INFORMATION: Mouse heavy g1 constant region

<400> SEQUENCE: 30

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190
```

```
Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225             230                 235                 240

Ser Leu Thr Cys Met Ile Thr Asp Phe Phe Pro Glu Asp Ile Thr Val
            245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
            275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305             310                 315                 320

Ser Pro Gly Lys

<210> SEQ ID NO 31
<211> LENGTH: 102
<212> TYPE: PRT
<213> ORGANISM: Artificial Sequence
<220> FEATURE:
<223> OTHER INFORMATION: Mouse heavy g1 Fab no hinge constant region

<400> SEQUENCE: 31

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys
            100

<210> SEQ ID NO 32
<211> LENGTH: 107
<212> TYPE: PRT
<213> ORGANISM: Artificial Sequence
<220> FEATURE:
<223> OTHER INFORMATION: Mouse light chain constant region

<400> SEQUENCE: 32

Arg Thr Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60
```

```
Thr Tyr Ser Met Ser Ser Thr Leu Thr Leu Thr Lys Asp Glu Tyr Glu
 65                  70                  75                  80

Arg His Asn Ser Tyr Thr Cys Glu Ala Thr His Lys Thr Ser Thr Ser
                 85                  90                  95

Pro Ile Val Lys Ser Phe Asn Arg Asn Glu Cys
            100                 105
```

<210> SEQ ID NO 33
<211> LENGTH: 107
<212> TYPE: PRT
<213> ORGANISM: Artificial Sequence
<220> FEATURE:
<223> OTHER INFORMATION: Light chain constant region

<400> SEQUENCE: 33

```
Arg Thr Val Ala Ala Pro Ser Val Phe Ile Phe Pro Pro Ser Asp Glu
 1               5                   10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 34
<211> LENGTH: 103
<212> TYPE: PRT
<213> ORGANISM: Artificial Sequence
<220> FEATURE:
<223> OTHER INFORMATION: Heavy chain gamma 1 Fab CH1 no hinge constant
      region

<400> SEQUENCE: 34

```
Ala Ser Thr Lys Gly Pro Ser Val Phe Pro Leu Ala Pro Ser Ser Lys
 1               5                   10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys
            100
```

<210> SEQ ID NO 35
<211> LENGTH: 330
<212> TYPE: PRT
<213> ORGANISM: Artificial Sequence
<220> FEATURE:
<223> OTHER INFORMATION: Heavy chain gamma 1 full length constant region

<400> SEQUENCE: 35

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 36
<211> LENGTH: 327
<212> TYPE: PRT
<213> ORGANISM: Artificial Sequence
<220> FEATURE:
<223> OTHER INFORMATION: Heavy chain gamma 4 full length constant region

<400> SEQUENCE: 36

```
Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 37
<211> LENGTH: 327
<212> TYPE: PRT
<213> ORGANISM: Artificial Sequence
<220> FEATURE:
<223> OTHER INFORMATION: Heavy chain gamma 4P full length constant
      region

<400> SEQUENCE: 37

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

-continued

```
Gly Val His Thr Phe Pro Ala Val Leu Gln Ser Ser Gly Leu Tyr Ser
 50                  55                  60
Leu Ser Ser Val Val Thr Val Pro Ser Ser Ser Leu Gly Thr Lys Thr
 65                  70                  75                  80
Tyr Thr Cys Asn Val Asp His Lys Pro Ser Asn Thr Lys Val Asp Lys
                 85                  90                  95
Arg Val Glu Ser Lys Tyr Gly Pro Pro Cys Pro Pro Cys Pro Ala Pro
                100                 105                 110
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
            130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
                180                 185                 190
Trp Leu Asn Gly Lys Glu Tyr Lys Cys Lys Val Ser Asn Lys Gly Leu
            195                 200                 205
Pro Ser Ser Ile Glu Lys Thr Ile Ser Lys Ala Lys Gly Gln Pro Arg
            210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
                260                 265                 270
Thr Thr Pro Pro Val Leu Asp Ser Asp Gly Ser Phe Phe Leu Tyr Ser
            275                 280                 285
Arg Leu Thr Val Asp Lys Ser Arg Trp Gln Glu Gly Asn Val Phe Ser
            290                 295                 300
Cys Ser Val Met His Glu Ala Leu His Asn His Tyr Thr Gln Lys Ser
305                 310                 315                 320
Leu Ser Leu Ser Leu Gly Lys
                325
```